US012586673B2

(12) United States Patent
Boufahja et al.

(10) Patent No.: US 12,586,673 B2
(45) Date of Patent: Mar. 24, 2026

(54) SYSTEMS AND METHODS FOR RADIATION ENTRY IN DOSE MANAGEMENT

(71) Applicant: GE Precision Healthcare LLC, Wauwatosa, WI (US)

(72) Inventors: Abderrazek Boufahja, Illkirch-Graffenstaden (FR); Philippe Muller, Lingolsheim (FR); Christophe Payet, Strasbourg (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 416 days.

(21) Appl. No.: 18/305,017

(22) Filed: Apr. 21, 2023

(65) Prior Publication Data

US 2024/0355449 A1 Oct. 24, 2024

(51) Int. Cl.
*G16H 20/40* (2018.01)
*A61N 5/00* (2006.01)

(52) U.S. Cl.
CPC .............. *G16H 20/40* (2018.01); *A61N 5/00* (2013.01)

(58) Field of Classification Search
None
See application file for complete search history.

(56) References Cited

U.S. PATENT DOCUMENTS

| | | | | |
|---|---|---|---|---|
| 2012/0106817 A1* | 5/2012 | Shih | ...................... | A61B 6/583 |
| | | | | 382/131 |
| 2020/0335199 A1* | 10/2020 | Accomazzi | .............. | G06N 3/08 |
| 2024/0266016 A1* | 8/2024 | Mirkar | ................... | G16H 30/20 |
| 2024/0347156 A1* | 10/2024 | Paulett | ................... | G16H 30/40 |

FOREIGN PATENT DOCUMENTS

| | | | | | |
|---|---|---|---|---|---|
| CN | 110957014 A | * | 4/2020 | ............. | G06Q 10/02 |
| KR | 100696708 B1 | * | 3/2007 | ............. | G16H 10/00 |
| KR | 102358038 B1 | * | 2/2022 | ............. | G16H 50/70 |

OTHER PUBLICATIONS

Pan et al. (CN-110957014-A) English Translation (Year: 2020).*
Jonghyo Kim (KR-100696708-B1) English Translation (Year: 2007).*

(Continued)

*Primary Examiner* — Miya J Cato
(74) *Attorney, Agent, or Firm* — McCoy Russell LLP

(57) ABSTRACT

Various methods and systems are provided for agnostic transmission of radiation information data. In one example, a radiation manual entry tool (RMET) includes a worklist access component series configured to receive via a network a first user input requesting access to a modality worklist, transform the first user input from a first format to a second format, transmit the first user input via the network, and receive a requested modality worklist via the network. The RMET further includes a data submission component series configured to receive via the network a second user input including radiation dose information manually entered into the requested modality worklist, transform the second user input from the first format to the second format, transmit the second user input via the network, and receive a message via the network confirming receipt of the manually entered radiation dose information for a scheduled procedure of the requested modality worklist.

20 Claims, 13 Drawing Sheets

(56) References Cited

OTHER PUBLICATIONS

Kim Young-Geun et al. (KR-102358038 / KR-20200037151A) Merged Translation (Year: 2022).*

Cook, T. et al., "Informatics in Radiology: RADIANCE: An Automated, Enterprise-wide Solution for Archiving and Reporting CT Radiation Dose Estimates," RadioGraphics, vol. 31, No. 7, Nov. 8, 2011, 15 pages.

Gress, D. et al., "AAPM medical physics practice guideline 6.a.: Performance characteristics of radiation dose index monitoring systems," Journal of Applied Clinical Medical Physics, vol. 18, No. 4, Jul. 2017, 11 pages.

"Radimetrics 2.9A User Guide," Bayer Radiology Website, Available Online at https://www.radiology.bayer.com/sites/g/files/vrxlpx8576/files/2020-08/84135038-RevM-RadimetricsUserGuide-V2.9A.pdf, Available as Early as Aug. 2020, 289 pages.

Loose. R. et al., "Radiation dose management systems—requirements and recommendations for users from the ESR EuroSafe Imaging initiative," European Radiology, vol. 31, No. 4, Apr. 2021, 9 pages.

"Radiation Dose Summary for Diagnostic Procedures on FHIR," HLZ International Website, Available Online at http://hl7.org/fhir/uv/radiation-dose-summary/2022Jan/, Jan. 2022, 2 pages.

Ria, F. et al., "Statement of the Italian Association of Medical Physics (AIFM) task group on radiation dose monitoring systems," Insights into Imaging, vol. 13, No. 1, Feb. 5, 2022, 9 pages.

Fisher, R. et al., "AAPM Medical Physics Practice Guideline 12.a: Fluoroscopy dose management," Journal of Applied Clinical Medical Physics, vol. 23, No. 3, Mar. 2022, 19 pages.

"Manual input of historical data," BitBucket Website, Available Online at https://bitbucket.org/openrem/openrem/issues/943/manual-input-of-historical data, Available as Early as Jul. 25, 2022, 5 pages.

Lindop, C., "FHIR Imaging Service Request Resource Mapping," Confluence HL7 Website, Available Online at https://confluence.hl7.org/display/IMIN/FHIR+Imaging+Service+Request+Resource+Mapping, Available as Early as Nov. 22, 2022, 6 pages.

* cited by examiner

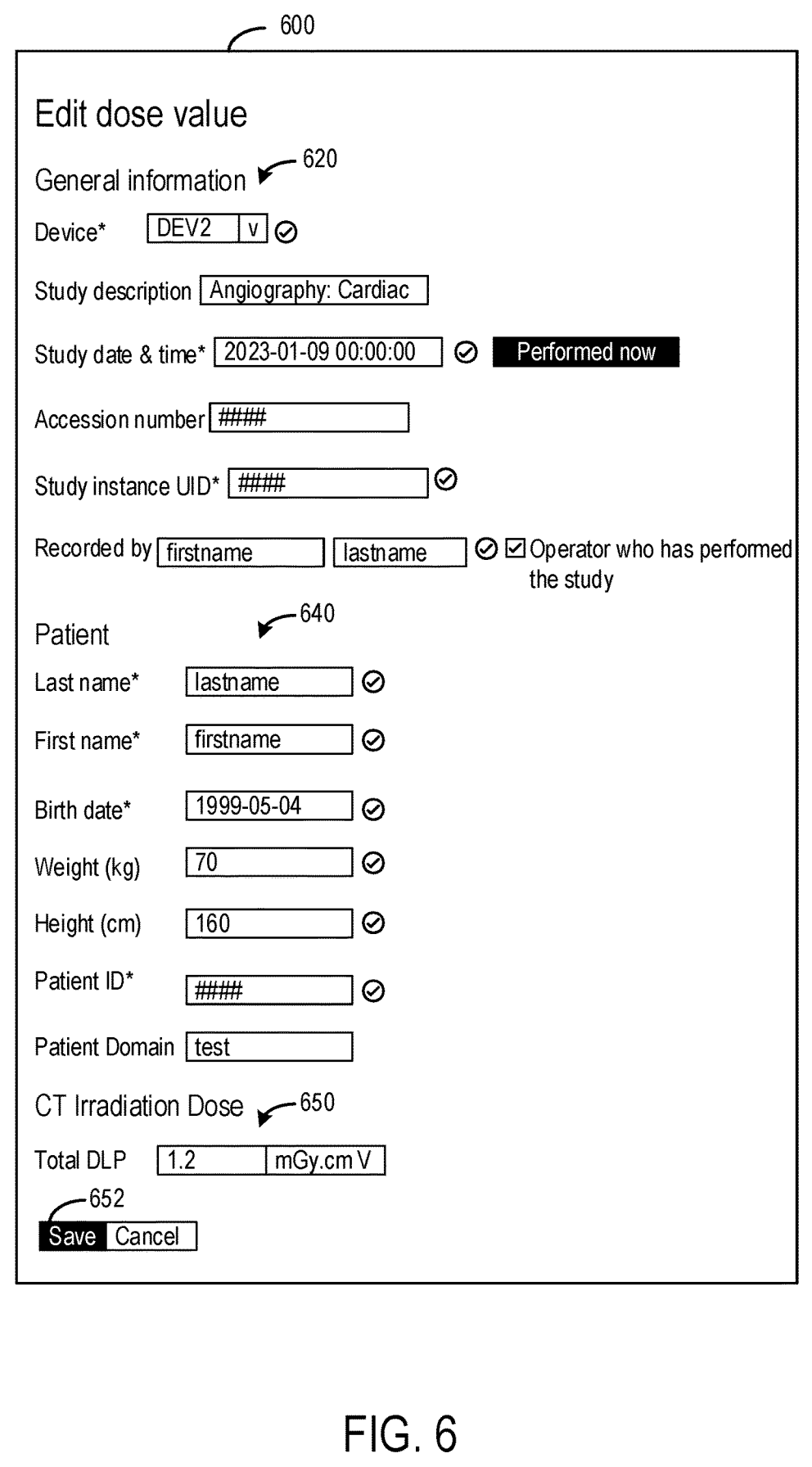

— 600

Edit dose value

General information ✔— 620

Device*  [DEV2  |v]  ⊘

Study description  [Angiography: Cardiac]

Study date & time*  [2023-01-09 00:00:00]  ⊘  [Performed now]

Accession number  [####]

Study instance UID*  [####]  ⊘

Recorded by  [firstname]  [lastname]  ⊘  ☑ Operator who has performed
the study

Patient  ✔— 640

Last name*  [lastname]  ⊘

First name*  [firstname]  ⊘

Birth date*  [1999-05-04]  ⊘

Weight (kg)  [70]  ⊘

Height (cm)  [160]  ⊘

Patient ID*  [####]  ⊘

Patient Domain  [test]

CT Irradiation Dose  ✔— 650

Total DLP  [1.2]  [mGy.cm V]

— 652
[Save] [Cancel]

FIG. 6

SYSTEMS AND METHODS FOR RADIATION ENTRY IN DOSE MANAGEMENT

FIELD

Examples of the subject matter disclosed herein relate to radiation analytics and management through agnostic transmission of medical data.

BACKGROUND

Medical data and radiation information collected by irradiating modalities for delivering radiation to patients is commonly stored in a database of a radiation dose management system. Some irradiating modalities may be configured to interact solely with dose management systems and databases thereof which use a certain format for data configuration. For example, irradiating modalities may be coupled to a specific provider of a radiation dose management system. When irradiation modalities are configured by a manufacturer of the radiation dose management system to enable direct communication therebetween, operation of the irradiation modalities may be exclusive to the radiation dose management system, which may lead to delays and/or cumbersome processes when the radiation dose management system is updated. Additionally, this may cause network traffic and complexity when a healthcare system (e.g., a hospital) includes irradiation modalities configured to communicate using different formats for data configuration than that of a radiology information system and/or dose management system.

Some irradiating modalities may not include components for automatically outputting medical data and radiation information to dose management systems, and therefore may not be configured to interact with dose management systems. In these embodiments, hospitals may manage the radiation data performed on patients through manual data entry, by manually reading the radiation data from a console of the irradiating modality, and manually reporting the radiation data in data files. The manually recorded data may be input into a dose management system via a proprietary manual entry (ME) component. However, not all dose management systems comprise a ME component, and there is no known standalone radiation manual entry application which can connect agnostically to any dose management system using standardized data transfer methods.

BRIEF DESCRIPTION

In one example, a system for agnostic transmission of radiation dose data comprises a radiation manual entry tool (RMET) having a worklist access component series configured to receive via a network a first user input requesting access to a modality worklist, transform the first user input from a first format to a second format, transmit the first user input via the network to a radiology information system (RIS) operably coupled to the network, and receive a requested modality worklist from the RIS via the network. The RMET further comprises a data submission component series configured to receive via the network a second user input including manually entered radiation dose information, transform the second user input from the first format to the second format, transmit the second user input via the network to a dose management system (DMS) operably coupled to the network, and receive a message via the network confirming receipt of the manually entered radiation dose information for a scheduled procedure of the requested modality worklist.

A method for agnostic transmission of medical data which may be executed by the RMET comprises receiving a first user input in a first format via a network, the first user input requesting access to a modality worklist, transforming the first user input in the first format to a second format, transmitting the first user input in the second format via the network to access a requested modality worklist, and receiving the requested modality worklist via the network. A user may interact with the received modality worklist via a user interface and manually enter radiation dose data as a second user input. The method further comprises receiving a second user input in the first format via the network, the second user input including manually entered radiation dose information for a scheduled procedure of the requested modality worklist, transforming the second user input in the first format to the second format, transmitting the second user input in the second format via the network to submit the manually entered radiation dose information for the scheduled procedure of the modality worklist, and receiving a message confirming receipt of the manually entered radiation dose information for the scheduled procedure.

The RMET may be used in a medical environment, the medical environment comprising a workstation displaying a user interface and operably coupled to a network, a RIS operably coupled to the network, a DMS operably coupled to the network, and the RMET. The RMET is configured to receive a first user input in a first format requesting access to a modality worklist from the workstation via the network, transform the first user input to a second format and/or a third format, transmit the first user input to the RIS via the network, receive a requested modality worklist from the RIS, receive from the workstation via the network a second user input in the first format, the second user input including manually entered radiation dose information for a scheduled procedure of the requested modality worklist, transforming the second user input in the first format to the second format and/or the third format, transmit information from the second user input to the DMS via the network, and receive a message from the DMS confirming receipt of the manually entered radiation dose information for the scheduled procedure.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting examples, with reference to the attached drawings, wherein below:

FIG. 6 shows a second example user interface used to share manually entered radiation dose data;

DETAILED DESCRIPTION

Described herein are methods and systems for agnostic transmission of manually entered radiation dose data to a dose management system (DMS). Given that some irradiating modalities are not configured to transmit data to a DMS, and some DMS do not comprise manual entry (ME) components, a radiation manual entry tool (RMET) is introduced herein. The RMET comprises components that enable agnostic communication with elements of a medical system to transmit radiation dose data to a DMS. The methods and systems described herein enable the DMS to receive and store radiation dose data from irradiating modalities which are not configured to directly communicate with the DMS. This may enable the DMS to store an increased amount of data.

Some DMS may include a ME tool, however the existing ME tool may present challenges in communication with third-party tools. For example, communication between front-end and back-end components of the existing ME tool may be a proprietary application programming interface (API). Manually entered data may be packaged with proprietary tags which may not be understood by third-party DMS. The RMET described herein enables sharing of manually entered radiation dose data to different stakeholders by using standardized methods to collect, transform, and share data, thus improving an interoperability and a quality of shared data.

Figure 1:
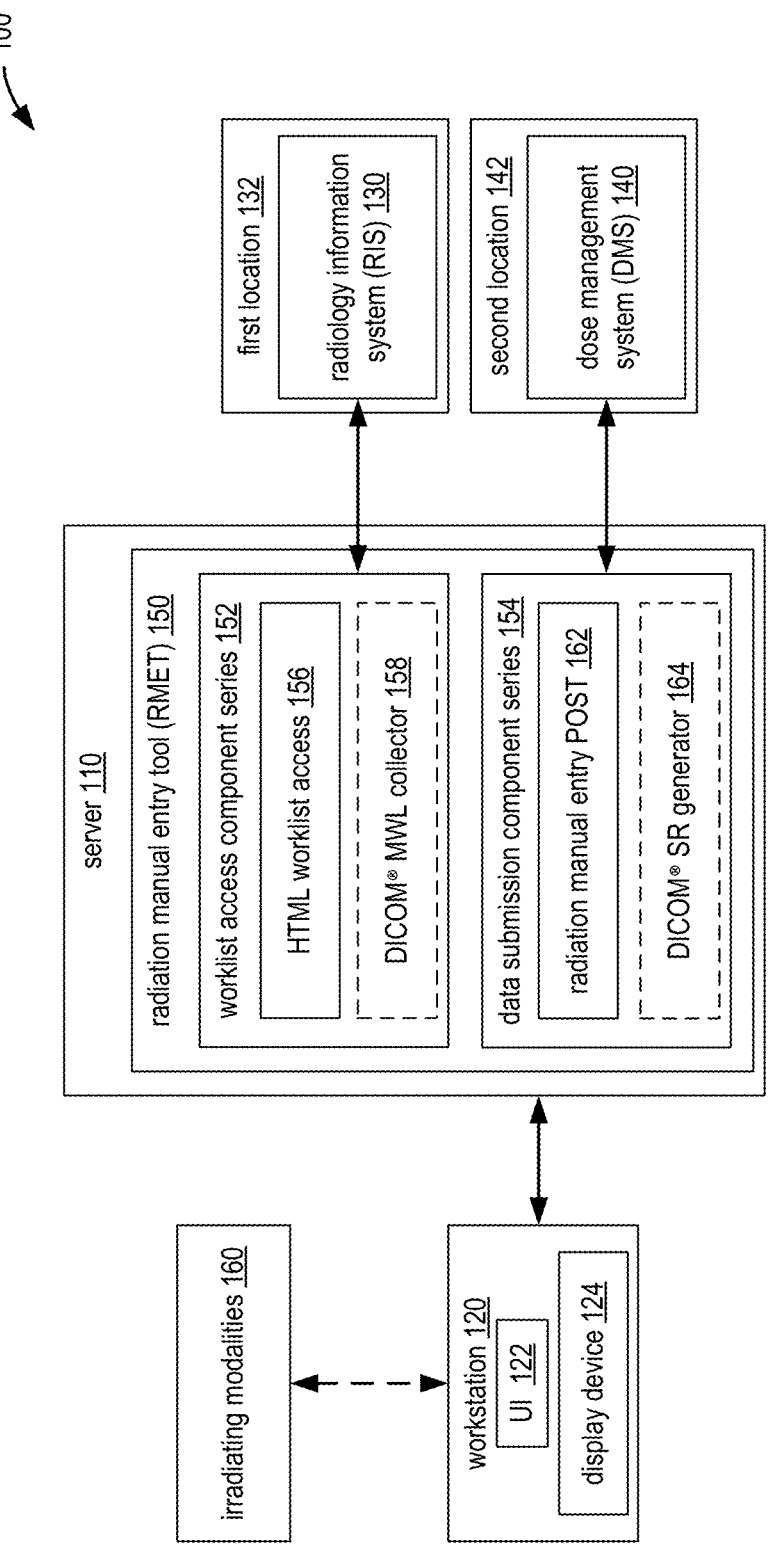
FIG. 1 shows a schematic block diagram of a medical environment, including a radiation manual entry tool (RMET)
Figure 2A:
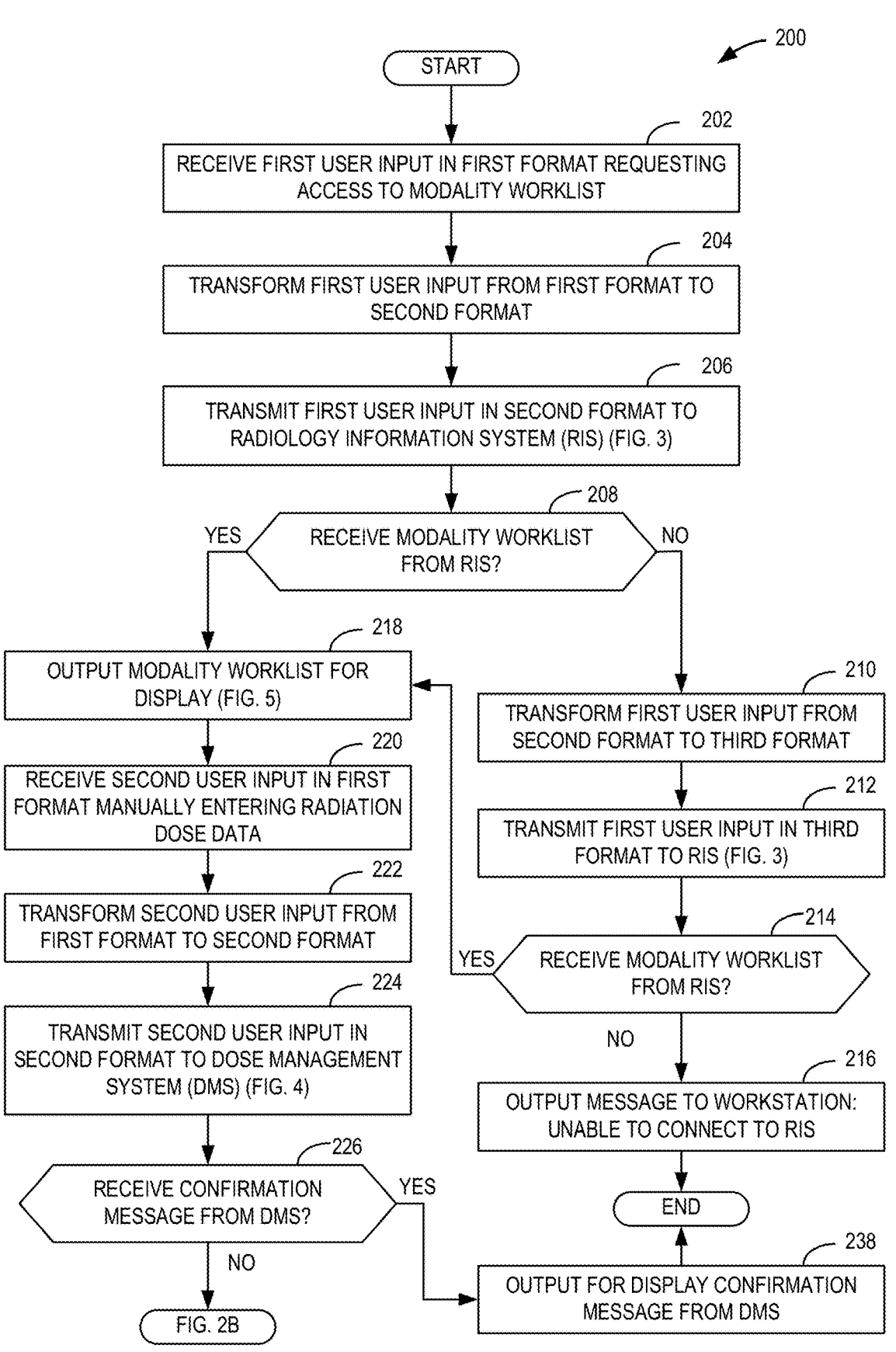
FIGS. 2A-2B illustrate a method of the RMET for submitting manually entered data to a dose management system (DMS)
Figure 2B:
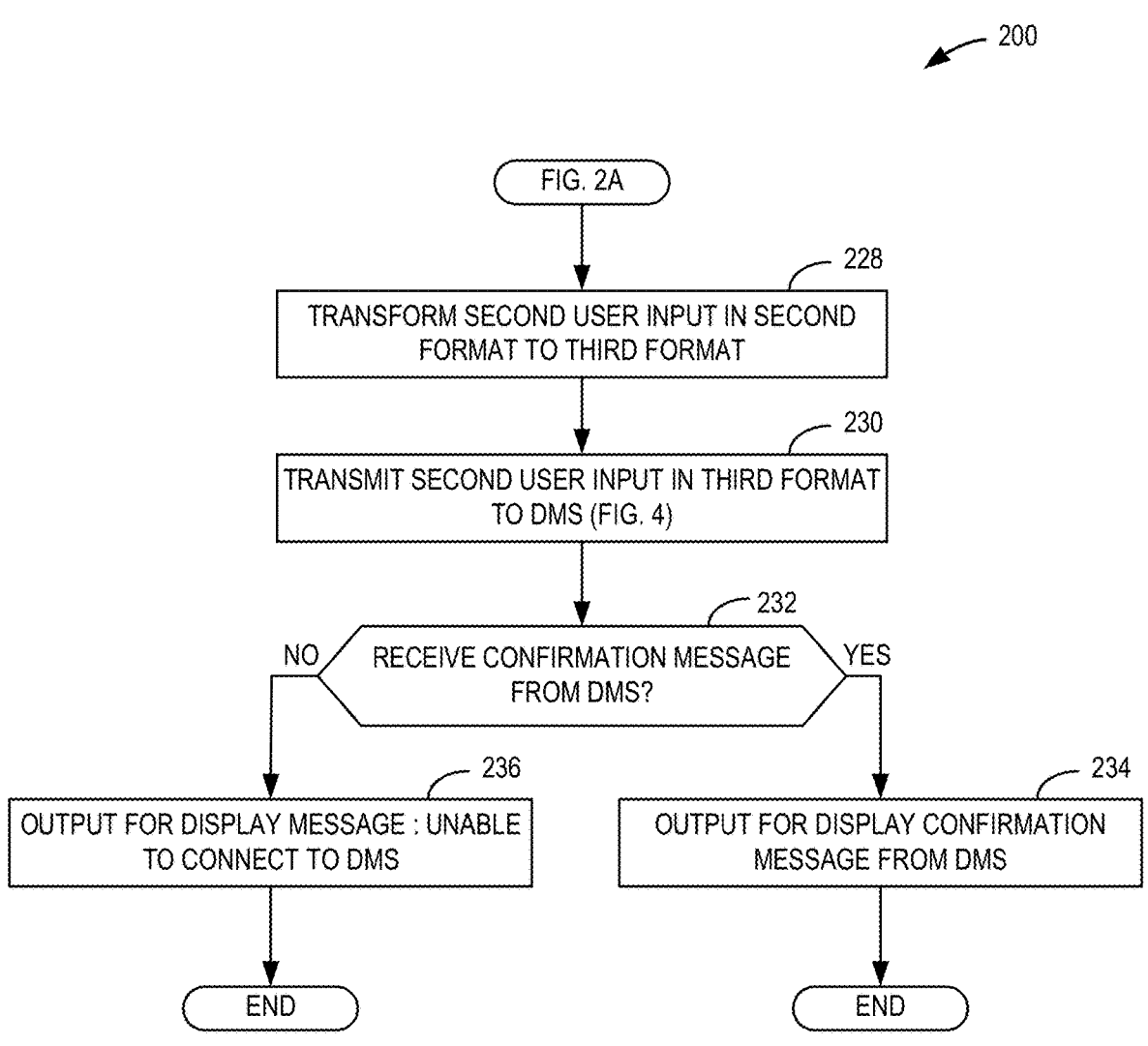
Figure 3:
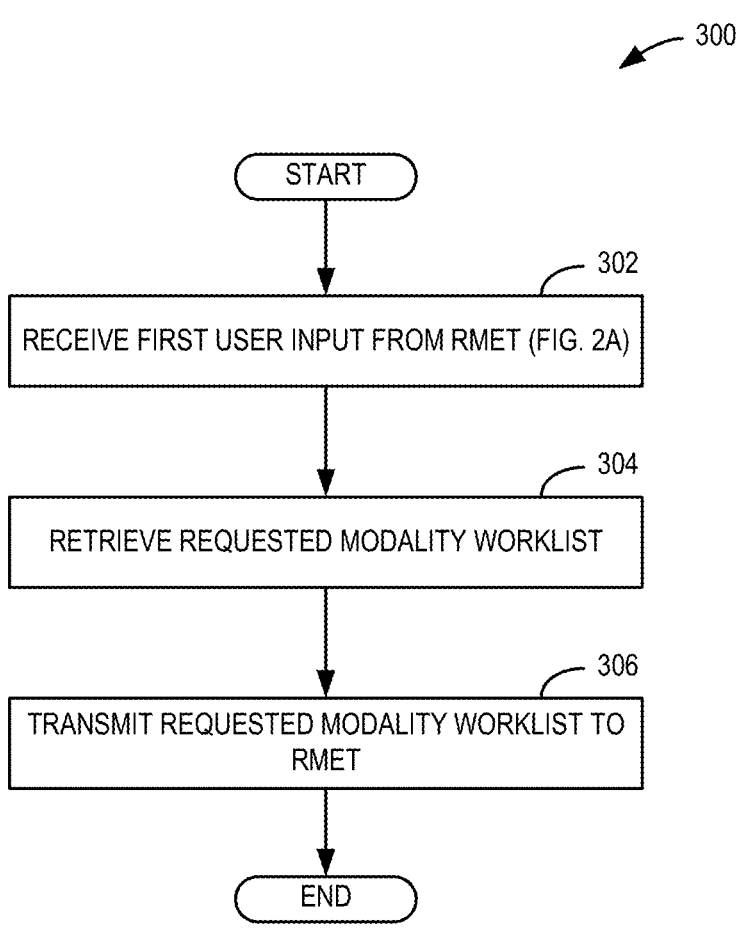
FIG. 3 illustrates a method of a radiology information system (RIS) for transmitting a modality worklist to the RMET.
Figure 4:
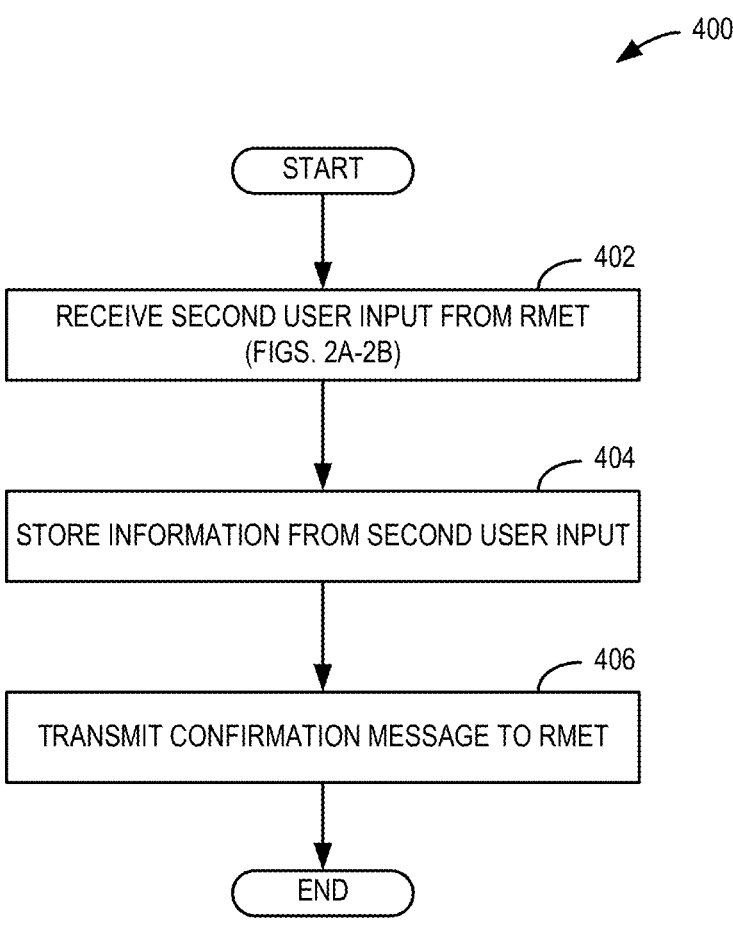
FIG. 4 illustrates a method of the DMS for receiving manually entered data from the RMET.
Figure 5:
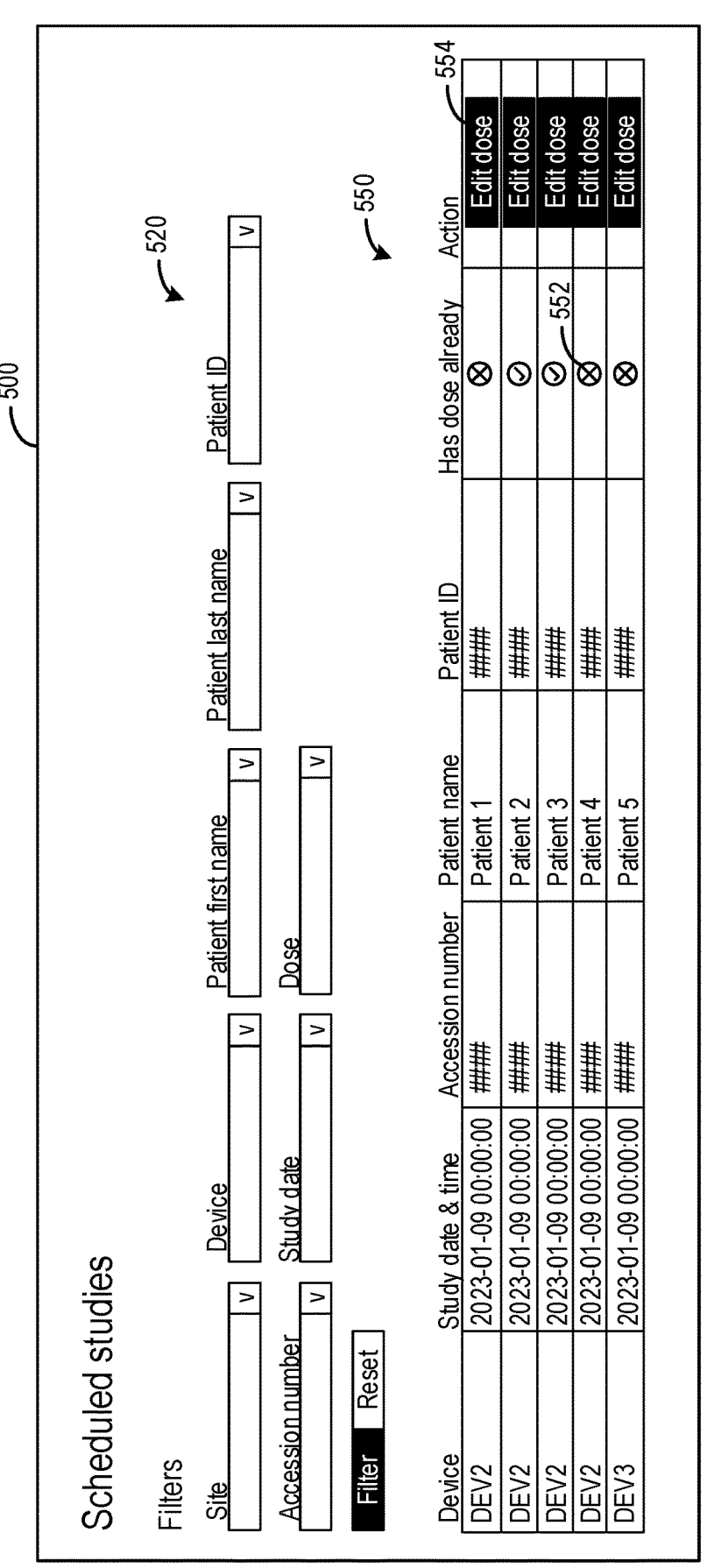
FIG. 5 shows a first example user interface used to access a scheduled worklist and share radiation dose data.
Figure 7:
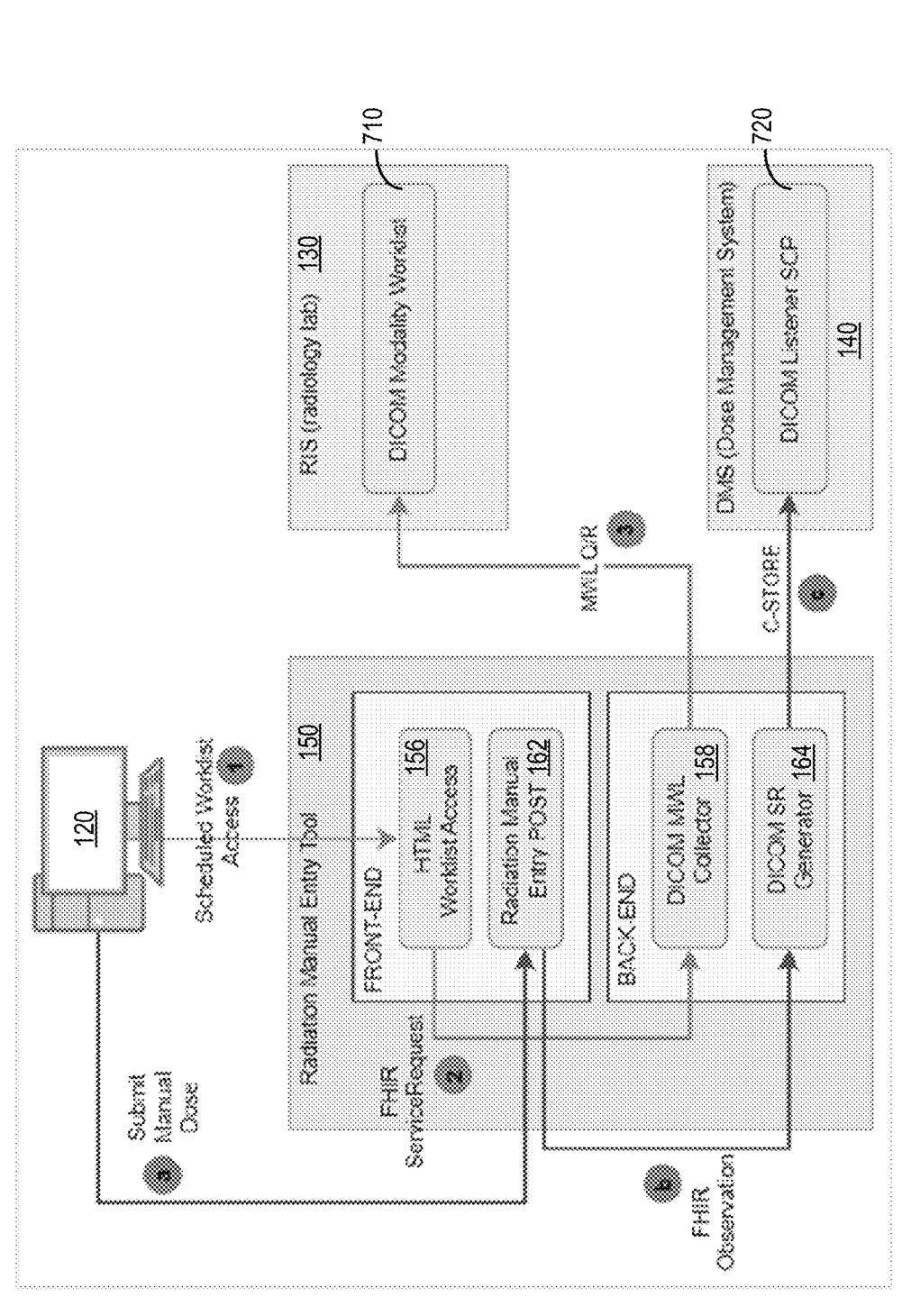
FIG. 7 shows an example configuration of a Digital Imaging and Communications in Medicine (DICOM®)-based manual entry method.
Figure 8:
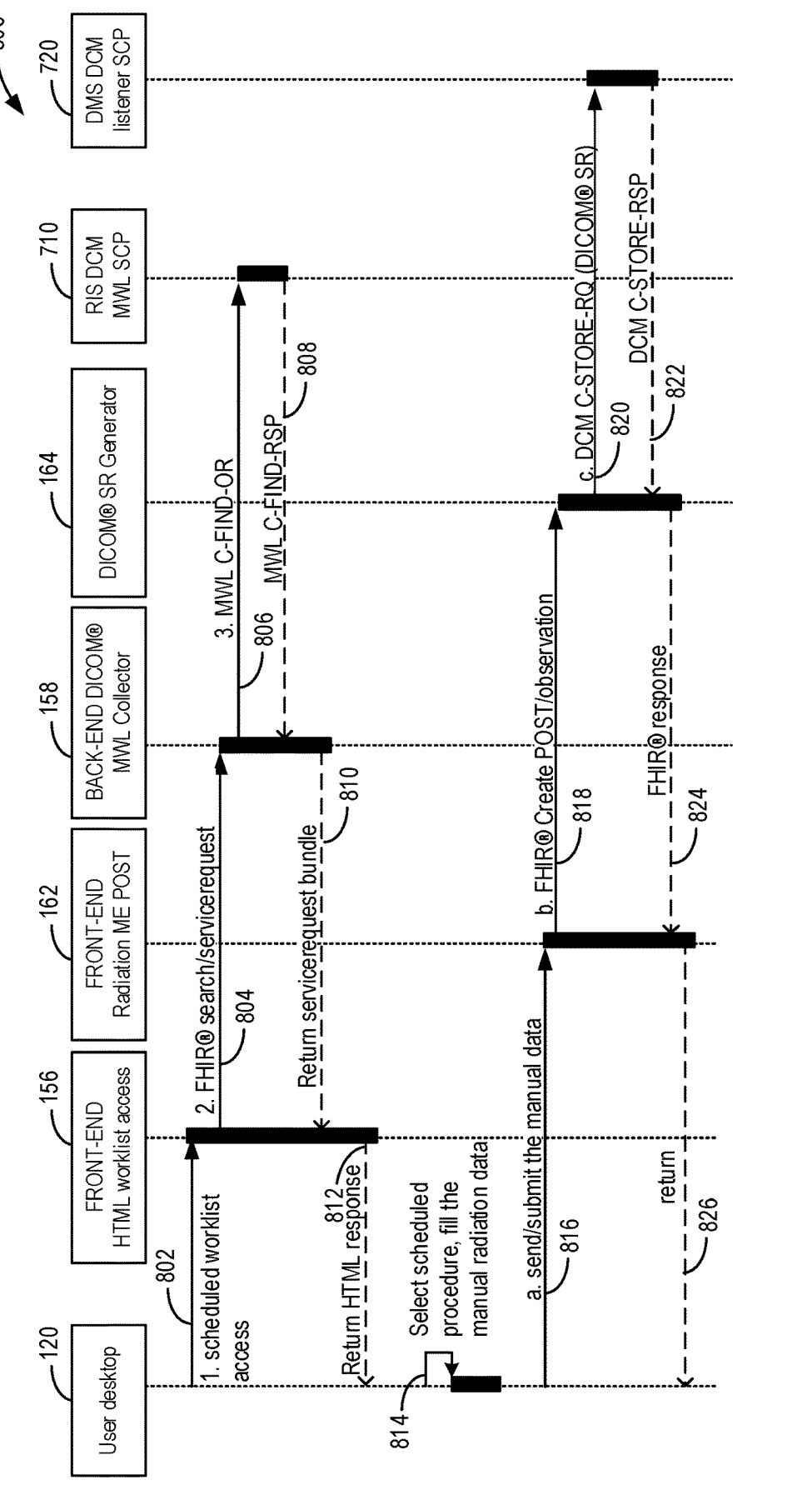
FIG. 8 shows a first example sequence diagram for the DICOM®-based manual entry method.
Figure 9:
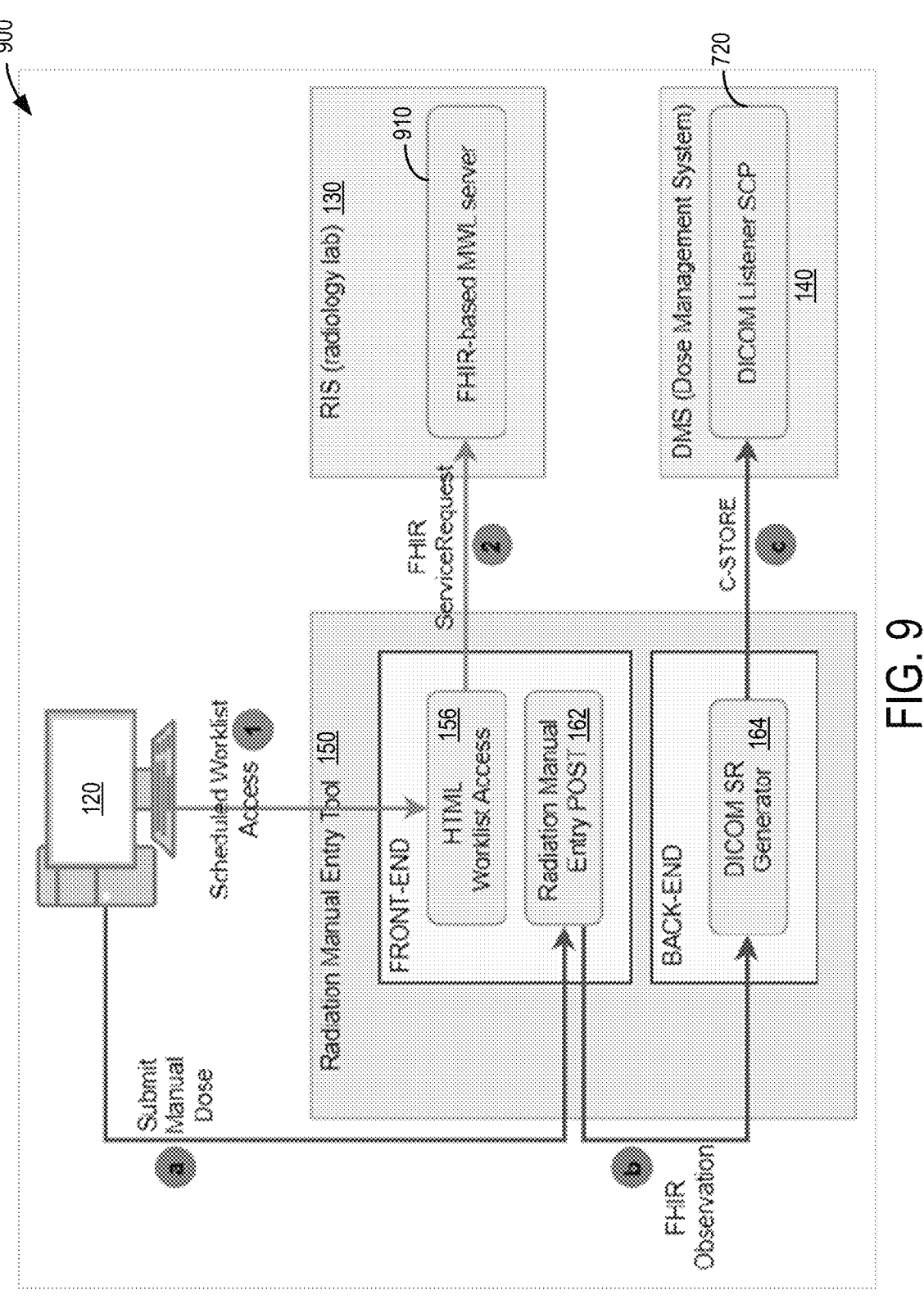
FIG. 9 shows an example configuration of a mixed Fast Healthcare Interoperability Resources (FHIR®)/DICOM®-based manual entry method.
Figure 10:
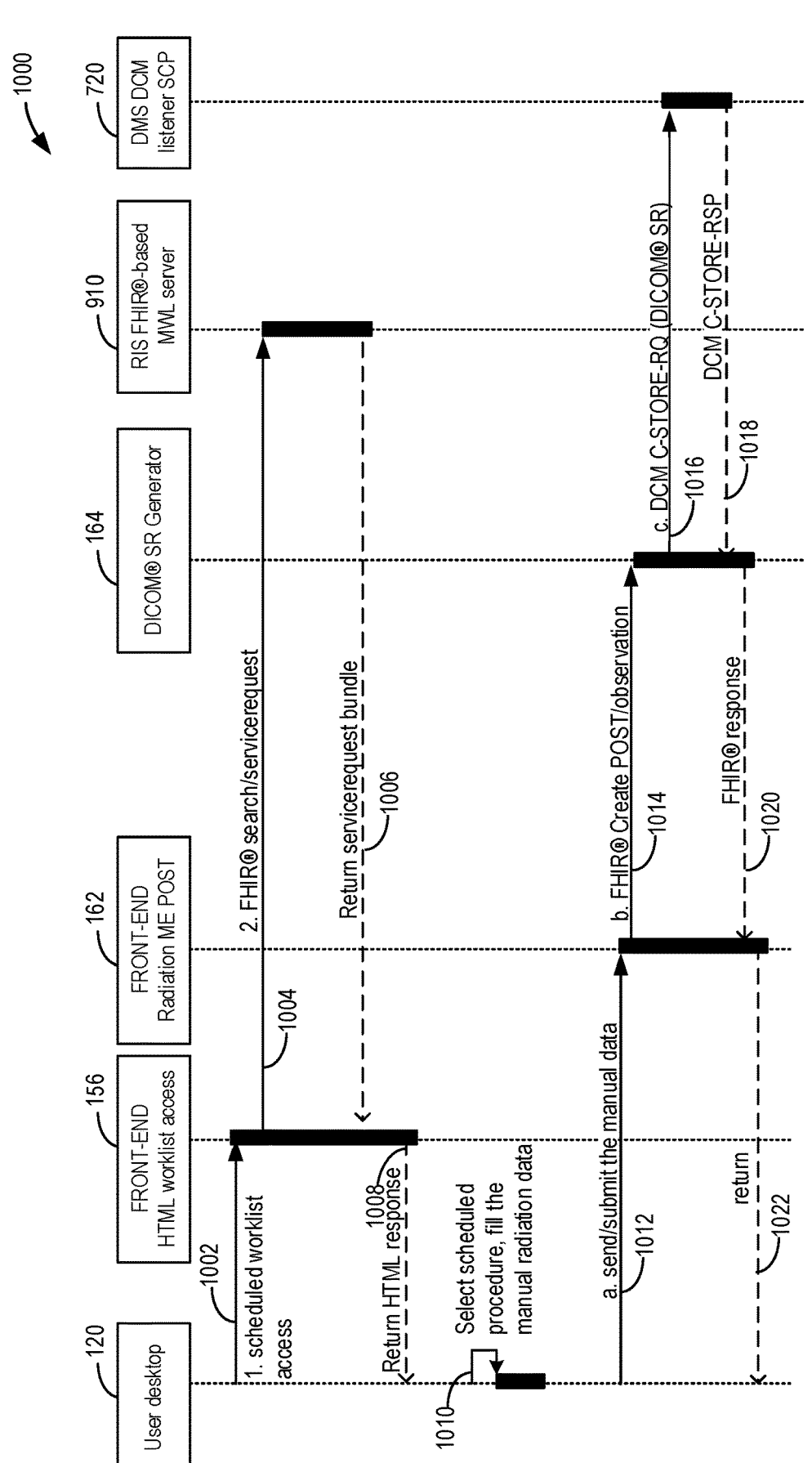
FIG. 10 shows a second example sequence diagram for the mixed FHIR®/DICOM®-based manual entry method.
Figure 11:
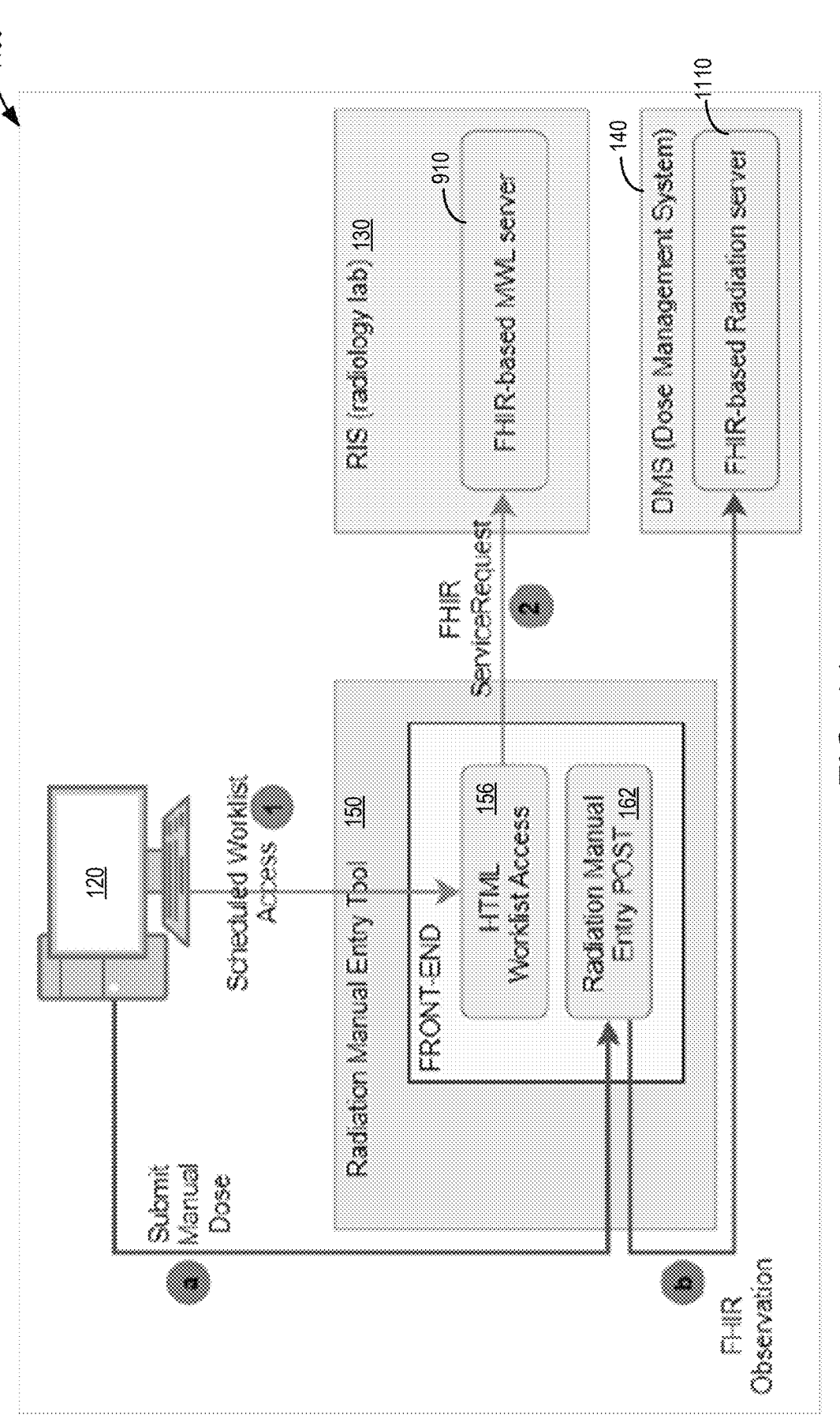
FIG. 11 shows an example configuration of a FHIR®-based manual entry method.
Figure 12:
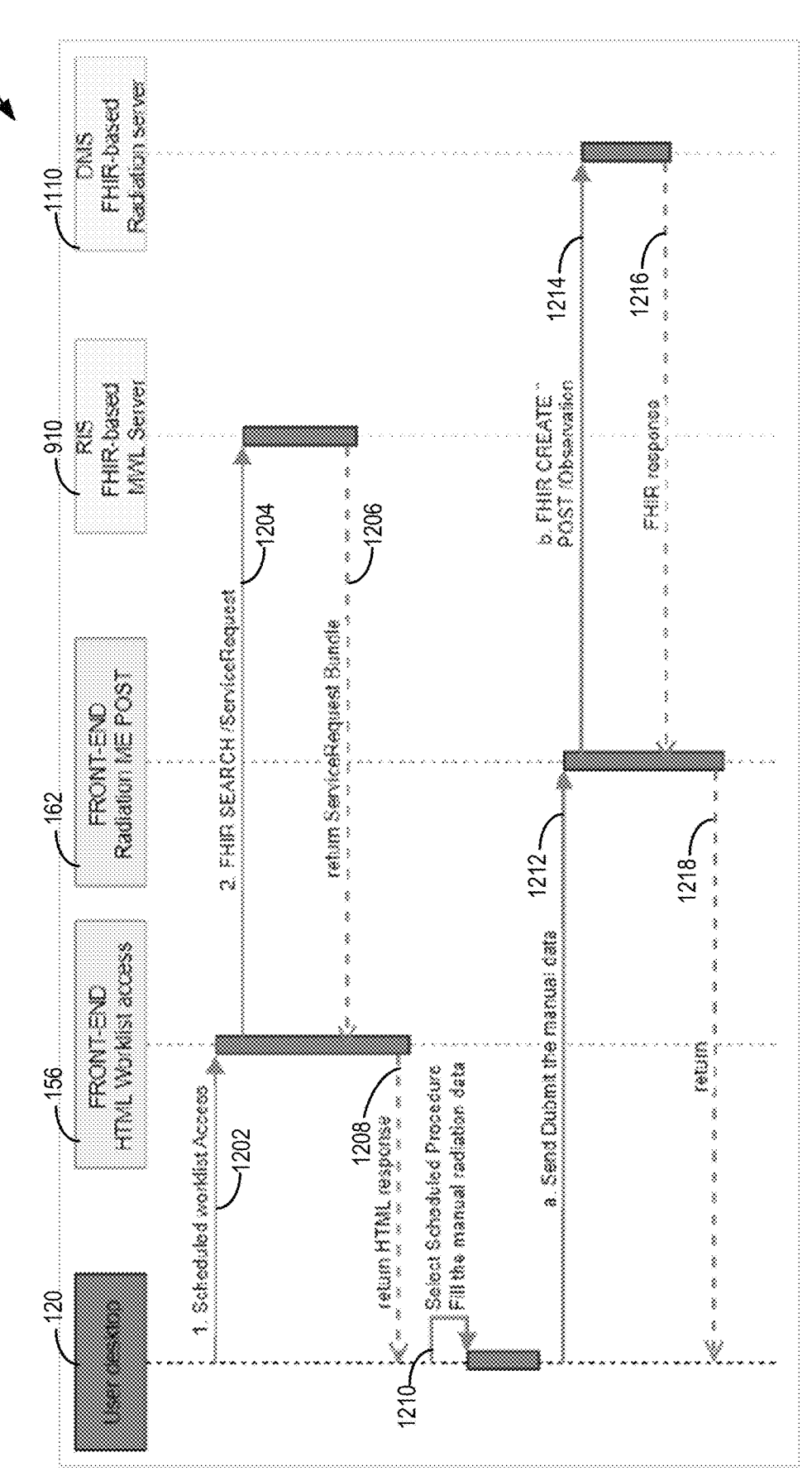
FIG. 12 shows a third example sequence diagram for the FHIR®-based manual entry method.

FIG. 1 shows a medical environment in which a RMET may be deployed. The medical environment includes the RMET, a workstation via which a user may input radiation dose data, a radiology information system (RIS) storing modality worklists, and a DMS storing radiation dose data. FIGS. 2A-2B illustrate a method of the RMET for requesting access to a modality worklist from the RIS and submitting manually entered radiation dose data to the DMS. FIG. 3 illustrates a method of the RIS for delivering the modality worklist to the RMET, and FIG. 4 illustrates a method of the DMS for receiving the manually entered radiation dose data from the RMET. FIG. 5 shows a first example user interface, which may be displayed at the workstation and accessed by a user to access a modality worklist. FIG. 6 shows a second example user interface, which may also be displayed at the workstation and accessed by a user to manually enter radiation dose data. The RIS and the DMS of the medical environment of FIG. 1 may comprise different formats for data configuration in different embodiments. For example, FIGS. 7 and 8 illustrate a method and a sequence diagram, respectively, for a Digital Imaging and Communications in Medicine (DICOM®)-based manual entry method. FIGS. 9 and 10 illustrate a method and a sequence diagram, respectively, for a mixed Fast Healthcare Interoperability Resources (FHIR®)/DICOM®-based manual entry method. FIGS. 11 and 12 illustrate a method and a sequence diagram, respectively, for a FHIR®-based manual entry method.

Turning to FIG. 1, a medical environment 100 is illustrated as a schematic block diagram. The medical environment 100 includes a RMET 150, which may be stored on a server 110 communicably coupled to a network of the medical environment 100 via wired and/or wireless connection. The RMET 150 comprises a plurality of components which may enable the RMET 150 to receive user inputs, transform data amongst different formats for data configuration, transmit data, and receive responses to transmitted data from other elements of the medical environment 100, as further described herein.

Also communicably connected to the network of the medical environment 100 is a user input system, such as a workstation 120 including a user interface (UI) 122 and a display device 124. As further described herein, a user may interact with the workstation 120 to submit user inputs to the RMET 150, such as a request for access to a modality worklist and a submission of manually entered radiation dose data. Also included in the medical environment 100 and communicably coupled to the network are a DMS 140 and a RIS 130. In some embodiments, the DMS 140 and the RIS 130 may each be stored at a location operably coupled to the network and remote from the server 110 on which the RMET 150 is stored. For example, the RIS 130 may be stored at a first location 132 and the DMS 140 may be stored at a second location 142. In some examples, the DMS 140 and the RIS 130 may be stored at the same location. As further described herein, each of the DMS 140 and the RIS 130 may use the same or different formats for data configuration, such as DICOM® and/or FHIR® standards. For example, the RIS 130 may be a radiology lab including a DICOM® modality worklist (MWL) server and/or a FHIR®-based MWL server. FHIR® is a standard for healthcare data exchange, published by Health Level Seven (HL7®), and defines a plurality of mechanisms used to exchange data continuously without losing or misinterpreting a meaning of the data during transmission between stakeholders. A FHIR® API may enable sharing of a summary of radiation procedures related to a specific patient using standardized FHIR® resources. This may assist third-parties in easily integrating data of the summary of radiation procedures into third-party applications without use of a DICOM® interpreter. DICOM® is a standard for communication and management of medical imaging information and related data, commonly used to store and transmit medical images and enable integration of medical imaging devices (e.g., irradiating modalities) from multiple manufacturers in the same medical environment. The RIS 130 may store at least one modality worklist, which is a scheduled worklist of procedures for a hospital modality such as an irradiating modality and/or imaging system. The DMS 140 may include a DICOM® listener service class provider (SCP) and/or a FHIR®-based radiation server. The DMS 140 may store medical data and radiation information, including radiation dose data, and may be communicably coupled to one or more third-party tools for analysis of radiation data.

The medical environment 100 may include one or more irradiating modalities 160 which collect radiation dose data that may be manually entered into the RMET 150. However, the one or more irradiating modalities 160 may not be communicably coupled to the network and/or to the DMS 140. For example, at least one of the one or more irradiating modalities 160 may not comprise DICOM® and/or FHIR® standards for radiation dose data output. An irradiating event may be performed by an irradiating modality of the one or more irradiating modalities 160, and radiation dose data may be read from a console of the irradiating modality and manually recorded (e.g., written down and/or entered into an Excel® file) by a user. Manually recorded data may be submitted to the DMS 140 via the RMET 150, as further described herein with respect to FIGS. 2A-2B.

The RMET 150 comprises a worklist access component series 152 and a data submission component series 154. The worklist access component series 152 is configured to receive, via the network, a first user input requesting access to a modality worklist, transform the first user input from a first format to a second format, transmit the first user input (e.g., in the second format) to the RIS 130 via the network, and receive a requested modality worklist from the RIS 130 via the network. In some embodiments the worklist access component series 152 is further configured to transform the first user input from the second format to a third format, depending on a format standard of the RIS 130 storing the requested worklist modality. The data submission component series 154 is configured to receive, via the network, a second user input including manually entered radiation dose data, transform the second user input from the first format to the second format, transmit the second user input to the DMS 140 via the network, and receive a message via the network confirming receipt of the manually entered radiation dose information for a scheduled procedure of the requested modality worklist by the DMS 140.

In some examples, such as configurations of the RMET 150 further described with respect to FIGS. 7-12, components of the worklist access component series 152 and the data submission component series 154 may be stored in a front-end and a back-end of the RMET 150. For example, the worklist access component series 152 includes a Hyper-Text Markup Language (HTML) worklist access component 156 and optionally a DICOM® MWL collector 158. The data submission component series 154 includes a radiation manual entry POST component 162 and optionally a DICOM® Structured Report (SR) generator 164. The HTML worklist access component 156 of the worklist access component series 152 and the radiation manual entry POST component 162 of the data submission component series 154 may be stored in the front-end, and the DICOM® MWL collector 158 of the worklist access component series 152 and the DICOM® SR generator 164 of the data submission component series 154 may be stored in the back-end. Communication between the front-end and back-end may be enabled by the FHIR® standard. Front-end components may communicate with the RIS 130 and/or the DMS 140 through standard FHIR® services. Back-end components may communicate with the RIS 130 and/or the DMS 140 through standard DICOM® message service element (DIMSE) services.

Components of each component series which are used to operably couple (e.g., transmit and receive data to/from) the RMET 150 to the RIS 130 and/or the DMS 140 may be automatically selected by a method of the RMET 150 based on a type of data format standard used by the RIS 130 and the DMS 140, as further described with respect to FIGS. 2A-2B. Briefly, one or more components of the back-end may not be used by the RMET 150 to transmit and/or receive data. For example, if a type of data format used by the DMS 140 is known, and a front-end component of the RMET 150 is configured with the type of data format used by DMS 140, the front-end component of the RMET 150 may be used and unused back-end components may not be loaded onto the server 110 storing the RMET 150. If a type of format of the DMS 140 is unknown, all components of the RMET 150 may be loaded onto the server 110 and, during operation as described herein with respect to FIGS. 2A-4, components of the back-end may be loaded onto the server 110 and/or activated as needed. This may reduce a processing demand of the RMET 150, compared to loading all back-end components even when some aren't used. In another example, all components of the back-end may be loaded regardless of whether the data format of the DMS 140 is known. In this way, if an additional DMS 140 with a different data format is added to the medical environment 100, the RMET 150 may already be configured to communicate with the additional DMS 140, which may reduce a downtime of data transmission to the new DMS 140, compared to if additional components of the RMET 150 had to be loaded onto the server 110.

As described herein, the RMET 150 comprises components which may enable the DMS 140 to receive radiation dose data from the one or more irradiating modalities 160 regardless of the output data format (or lack thereof) of the one or more irradiating modalities 160. Described another way, the RMET 150 enables agnostic sharing of manually entered data by using standardized methods to collect and share radiation dose data, improving an interoperability of the medical environment and improving a quality of the shared data. The RMET 150 may agnostically connect to any DMS using standardized data transfer methods and manually enter irradiation data into the DMS. Performance of the DMS may be increased, as systems and methods of the RMET 150 may enable the DMS 140 to receive and store irradiation data from more modalities than just those which output data in the same data format with which the DMS 140 is configured. This may further increase a network efficiency by reducing network traffic.

Turning to FIGS. 2A-2B, a method 200 is illustrated for requesting access to a modality worklist and submitting manually entered radiation dose data to a DMS. The method 200 described herein may be executed by the RMET 150 of FIG. 1, and thus references to a RIS and a DMS are to be interpreted as referring to the RIS 130 and the DMS 140 of FIG. 1. Instructions for the method 200 may be stored on a memory of the server 110 and executed by a processor of the workstation 120. The processor may receive inputs/requests/selections, as described herein, which may be input by a user via a UI (e.g., the UI 122 of the workstation 120 of FIG. 1).

At 202, the method 200 includes receiving a first user input in a first format, the first user input requesting access to a modality worklist. The first user input may be input by a user via a user interface, such as the UI 122 of the workstation 120 of FIG. 1. The first user input may be transmitted from the workstation 120 to the RMET via the network of the medical environment 100. Requesting access to a modality worklist may include interacting with the UI 122 and selecting an irradiating modality from a list of irradiating modalities (e.g., the one or more irradiating modalities 160 of FIG. 1), selecting a timeframe of the modality worklist, and so on. For example, the first user input may include a request for the RMET to retrieve a list of irradiating event/procedures performed by a first irradiating modality over a one-week span. The first format of the first user input may be HTML or other standard markup language for displayed documents.

At 204, the method 200 includes transforming the first user input from the first format to a second format. For example, the first user input may be received by the HTML worklist access component 156 of the worklist access component series 152, which may transform the first user input from the HTML format to a FHIR® standard format, such as a FHIR® ServiceRequest query. The first format may be an original format in which the first user input is submitted, via the workstation 120, such as HTML. The second format is a first standard data format configuration, herein the FHIR® standard format, which may be usable by the RIS 130 and/or the DMS 140. In other embodiments, other data format standards may be used by at least one of the workstation 120, the RIS 130, and the DMS 140, and elements of the RMET 150 which transform user inputs (e.g., the first user input and the second user input) from the first format to the second format and from the second format to the third format may be adjusted to elements which correspond to the other data format standards. As described herein, "transforming" user inputs from a first format to a second format and from a second format to a third format may include changing a structure, packaging, or other presentation of data of the user input while retaining the data information. For example, the HTML worklist access component 156 may include a library of commands (e.g., queries and responses) in both the HTML format and the FHIR® standard format, and thus be able to translate requests of the first user input from the HTML format to the FHIR® format, thus transforming data of the first user input from the first format to the second format.

In some embodiments of the medical environment 100, a data format of the RIS may be known to the RMET. For example, during an initial setup of the RMET (e.g., connection of the RMET to the network of the medical environment) and/or during connection of the RIS to the network of the medical environment, a type of data format used by the RIS may be submitted to the RMET. In these cases, as further described with respect to FIGS. 7-12, the first user input may be automatically converted from the first format to a format used by the RIS. For example, instead of sending the first user input in the second format to the RIS, where the RIS may be known to not accept the second format and thus a modality worklist may not be retrieved by the RIS, the first user input may be transformed from the first format to the second format, and from the second format to the third format prior to being transmitted to the RIS. Operation 204 of the method 200 may proceed to operation 210 without proceeding through operations 206-208. This may reduce a processing demand on the RMET and increase an efficiency of data transmission in the medical environment.

At 206, the method 200 includes transmitting the first user input, in the second format, to the RIS to request access to the modality worklist, which is stored on the RIS. Depending on a format for data configuration of the RIS, the RIS may or may not receive the first user input in a usable format. For example, if the RIS is configured to operate using FHIR® standards (e.g., the RIS comprises a FHIR®-based MWL server, as further described with respect to FIG. 11), the first user input as the FHIR® ServiceRequest query (e.g., in the second format) may be received by the RIS in a usable format. Details regarding receipt of the first user input from the perspective of the RIS are described with respect to FIG. 3. If the RIS is not configured to operate using FHIR® standards, the first user input as the FHIR® ServiceRequest query may not be received by the RIS in a usable format, and thus the RIS may not retrieve the requested modality worklist.

At 208, if it is determined that the RMET does not receive the requested modality worklist from the RIS, the method 200 proceeds to 210 to transform the first user input from the second format to a third format. The third format is a second standard data format configuration, herein the DICOM® standard format, which may be usable by the RIS 130 and/or the DMS 140. For example, in response to not receiving the requested modality worklist, the method 200 may determine that the first user input is not in a format usable by the RIS. A back-end component of the worklist access component series (e.g., the DICOM® MWL collector 158) may convert the first user input from the second format (e.g., FHIR® ServiceRequest query) to the third format (e.g., a DICOM® MWL query).

At 212, the method 200 includes transmitting the first user input in the third format to the RIS to again request access to the modality worklist. The RIS may or may not receive the first user input in a usable format. For example, if the RIS is configured to operate using DICOM® standards (e.g., the RIS comprises a DICOM® modality worklist, as further described with respect to FIG. 7), the first user input as the DICOM® MWL query (e.g., in the third format) may be received by the RIS in a usable format. Details regarding receipt of the first user input from the perspective of the RIS are described with respect to FIG. 3. If the RIS is not configured to operate using DICOM® standards, the first user input as the DICOM® MWL query may not be received by the RIS in a usable format, and thus the RIS may not retrieve the requested modality worklist.

At 214, if it is determined that the RMET does not receive the requested modality worklist from the RIS, the method 200 proceeds to 216 to output a message to the workstation (e.g., to the display device 124 of the workstation 120) that the RMET is unable to connect to the RIS. The method 200 ends.

Turning briefly to FIG. 3, a method 300 is shown for retrieving a requested modality worklist. The method 300 may be executed by the RIS 130 of FIG. 1. Instructions for the method 300 may be stored on a memory of RIS 130 and executed by a processor of the RIS 130. The processor may receive inputs/requests/selections, as described herein, which may be input by a user via a UI (e.g., the UI 122 of the workstation 120 of FIG. 1) and transmitted to the RIS 130 by the RMET 150 via the network of the medical environment 100.

At 302, the method 300 includes receiving the first user input from the RMET. As described with respect to FIGS. 2A-2B, the first user input may be transmitted to the RIS in the second format or in the third format. If the first user input is in a format which is different from the format with which the RIS is configured, the RIS may not receive the first user input. The RIS may receive the first user input at 302 when the format of the first user input is the same as the format with which the RIS is configured, as described above with respect to FIGS. 2A-2B.

At 304, the method 300 includes retrieving the requested modality worklist. The RIS may store (e.g., on the memory of the RIS) a plurality of worklists for a plurality of irradiating modalities of a respective environment in which the RIS is integrated. For example, a worklist for an irradiating modality may include an entry for each irradiating event which has been performed and/or is scheduled to be performed by the irradiating modality. The entry may include one or more of a device identifier (e.g., name, identification number, model, etc.), a date and time the study was or will be performed, a patient name and/or other patient identifier, a type of irradiating event, and an operator identifier. The first user input may request a modality worklist for an irradiating modality of a plurality of irradiating modalities (e.g., the one or more irradiating modality 160 of FIG. 1) for a given time frame, for example. The RIS may search stored worklists for the requested modality worklist and retrieve the requested modality worklist from storage.

At 306, the method 300 includes transmitting the requested modality worklist to the RMET. The requested modality worklist may be transmitted to the RMET in the data format of the RIS, which is also the data format of the first user input. For example, as further described with respect to FIGS. 7 and 8, if the first user input is transmitted to the RIS as a DICOM® MWL query, the requested modality worklist may be transmitted to the RMET as a DICOM® MWL response. The method 300 ends.

Returning to FIGS. 2A-2B, at 214 and at 208, if it is determined that the RMET does receive the requested modality worklist from the RIS, the method 200 proceeds to 218 to output the requested modality worklist for display (e.g., on the display device 124 of the workstation 120). An example display of the requested modality worklist is shown in and further described with respect to FIG. 5.

Turning briefly to FIG. 5, a first example display 500 is shown, comprising elements for accessing a requested modality worklist 550. The first example display 500 may be displayed on the display device 124 of the workstation 120, for example, and may include the requested modality worklist retrieved by the RMET 150 from the RIS 130, according to the methods described with respect to FIGS. 2A-2B and 3. The first example display 500 additionally includes filters 520 which may be used to select a desired entry or type of entries of the requested modality worklist 550. For example, the requested modality worklist 550 may be filtered by site (e.g., medical provider/location), device (e.g., individual device or type of device), patient, and so on. Filters 520 may be used to identify an irradiating event for which radiation dose data has been manually recorded (e.g., read from a console of the irradiating modality and entered into an Excel® file).

The requested modality worklist 550 includes a plurality of entries within parameters requested by the first user input (e.g., timeframe, device, operator, type of device, and so on). The requested modality worklist 550 includes columns for each of a device, study date and time, accession number, patient name, patient ID, whether the entry has dose information entered, and an action button 554. An indicator 552 may show whether dose information (e.g., radiation dose data) has been entered for a respective irradiating event. For example, a check mark may indicate that radiation dose data for the respective entry is included in the radiation information (e.g., has been transmitted to the DMS 140 using the RMET 150). An x mark may indicate that radiation dose data for the respective irradiating event has not been entered.

A user may interact with the UI (e.g., the UI 122 of the workstation 120) to select an irradiating event of the requested modality worklist 550 which does not have radiation information. For example, the user may select the action button 554, which may open a second display including more details of the selected irradiating event, as shown in FIG. 6.

FIG. 6 shows a second example display 600 comprising details of a selected irradiating event from the requested modality worklist, as described with respect to FIG. 5. The second example display 600 includes general information 620, such as a device name, a study description, and a study date and time, and patient information 640 including patient name, weight, and height. The second example display 600 further includes a manual entry box 650 for entering radiation dose data (e.g., total dose length product (DLP)) for the selected irradiating event. A user may manually enter radiation dose data which has been collected by an irradiating modality (e.g., the device indicated in the general information 620 section) into the manual entry box 650 and select a "save" button 652 to submit the radiation dose data to the DMS 140, as further described with respect to FIGS. 2A-2B, below. In some examples, selecting the "save" button 652 temporarily stores the manually entered radiation dose data and associated information (e.g., general information 620 and patient information 640), and returns to the first example display 500 of FIG. 5 where one or more additional irradiating events may be selected and corresponding radiation dose data may be manually entered in the same way as described with respect to FIG. 6. Following manual entry of radiation dose data for one or more irradiating events, a "submit" button (not shown in FIG. 5 or 6) may be selected to submit radiation dose data for the one or more irradiating events as a single user input to the DMS 140. This may assist in reducing network traffic and thus increasing an efficiency of the medical environment 100.

Returning to FIGS. 2A-2B, at 220, the method 200 includes receiving a second user input in the first format (e.g., HTML), the second user input including manually entered radiation dose data. For example, as described with respect to FIG. 6, the second user input may include radiation dose data and corresponding identifying information (e.g., patient identifying information, time and date of event, etc.) for one or more irradiating events of the requested modality worklist retrieved from the RIS. A user may interact with the UI of the workstation to input radiation dose data which was manually recorded from an irradiating modality, and submit the manually entered data and corresponding information to the RMET (e.g., by selecting the "save" or "submit" button, as described with respect to FIG. 6).

At 222, the method 200 includes transforming the second user input from the first format (e.g., HTML) to the second format. For example, the second user input may be received by the radiation manual entry POST component 162 of the data submission component series 154, which may transform the second user input from the HTML format to a FHIR® standard format, such as a FHIR® observation.

In some embodiments of the medical environment 100, a data format of the DMS may be known to the RMET. For example, during an initial setup of the RMET (e.g., connection of the RMET to the network of the medical environment) and/or during connection of the DMS to the network of the medical environment, a type of data format used by the DMS may be submitted to the RMET. In these cases, as further described with respect to FIGS. 7-12, the second user input may be automatically converted from the first format to a format used by the DMS. For example, instead of sending the second user input in the second format to the DMS, where the DMS may be known to not accept the second format and thus the radiation dose data may not be received by the DMS, the second user input may be transformed from the first format to the second format, and from the second format to the third format prior to being transmitted to the DMS. Operation 222 of the method 200 may proceed to operation 228 without proceeding through operations 224-226. This may reduce a processing demand on the RMET and increase an efficiency of data transmission in the medical environment.

At 224, the method 200 includes transmitting the second user input, in the second format, to the DMS to submit the manually entered radiation dose data to storage of the DMS. Depending on a format for data configuration of the DMS, the DMS may or may not receive the second user input in a usable format. For example, if the DMS is configured to operate using FHIR® standards (e.g., the DMS comprises a FHIR®-based radiation server, as further described with respect to FIG. 11), the second user input as the FHIR® observation (e.g., in the second format) may be received by the DMS in a usable format. Details regarding receipt of the second user input from the perspective of the DMS are described with respect to FIG. 4. If the DMS is not configured to operate using FHIR® standards, the second user input as the FHIR® observation may not be received by the DMS in a usable format, and thus the DMS may not receive the manually entered radiation dose data.

At 226, if it is determined that the RMET does receive the confirmation message from the DMS, the method 200 proceeds to 238 to output for display (e.g., on the display device 124 of the workstation 120) the confirmation message from the DMS indicating that the manually entered radiation dose data has been received by the DMS. The method 200 ends.

Turning briefly to FIG. 4, a method 400 is illustrated for receiving manually entered radiation dose data. The method 400 may be executed by the DMS 140 of FIG. 1. Instructions for the method 400 may be stored on a memory of DMS 140 and executed by a processor of the DMS 140. The processor may receive inputs/requests/selections, as described herein, which may be input by a user via a UI (e.g., the UI 122 of the workstation 120 of FIG. 1) and transmitted to the DMS 140 by the RMET 150 via the network of the medical environment 100.

At 402, the method 400 includes receiving the second user input from the RMET. As described with respect to FIGS. 2A-2B, the second user input may be transmitted to the DMS in the second format or in the third format. If the second user input is in a format which is different from the format with which the DMS is configured, the DMS may not receive the second user input. The DMS may receive the second user input at 402 when the format of the second user input is the same as the format with which the DMS is configured, as described above with respect to FIGS. 2A-2B.

At 404, the method 400 includes storing information from the second user input. For example, the DMS may store (e.g., on the memory of the DMS) radiation dose data and corresponding information, such as patient information and/or general information, as described with respect to FIG. 6.

At 406, the method 400 includes transmitting a confirmation message to the RMET. Following receipt and storage of the second user input, the DMS may generate the confirmation message in the data format of the DMS (e.g., in the same data format as the second user input), where the confirmation message may include text or other indication that the manually entered radiation dose data has been received by the DMS. The DMS transmits the confirmation message to the RMET via the network of the medical environment 100. The method 400 ends.

Returning to FIGS. 2A-2B, at 226, if it is determined that the RMET does not receive a confirmation message from the DMS, the method 200 proceeds to 228 (FIG. 2B) to transform the second user input from the second format (e.g., FHIR® standards) to the third format (e.g., DICOM® standards). For example, as described with respect to FIG. 4, upon receipt of the second user input by the DMS, the DMS may transmit a confirmation message to the RMET to indicate the radiation dose data has been received. If the RMET does not receive the confirmation message at 226, the method 200 may determine that the second user input in the second format may not be usable by the DMS. A back-end component of the data submission component series 154 (e.g., the DICOM® SR generator 164) may convert the second user input from the second format (e.g., FHIR® Observation®) to the third format (e.g., a DICOM® SR).

At 230, the method 200 includes transmitting the second user input in the third format to the DMS to store manually entered radiation dose data in the DMS. The DMS may or may not receive the second user input in a usable format. For example, if the DMS is configured to operate using DICOM® standards (e.g., the DMS comprises a DICOM® listener SCP, as further described with respect to FIG. 7), the second user input as the DICOM® SR (e.g., in the third format) may be received by the DMS in a usable format. Details regarding receipt of the second user input from the perspective of the DMS are described with respect to FIG. 4. If the DMS is not configured to operate using DICOM® standards, the second user input as the DICOM® SR may not be received by the DMS in a usable format, and thus the DMS may not store the manually entered radiation dose data and may not send the confirmation message to the RMET.

At 232, if it is determined that the RMET does not receive the confirmation message from the DMS, the method 200 proceeds to 236 to output a message to the workstation (e.g., to the display device 124 of the workstation 120) that the RMET is unable to connect to the DMS. The method 200 ends. At 232, if it is determined that the RMET does receive the confirmation message from the DMS, the method 200 proceeds to 234 to output for display (e.g., on the display device 124 of the workstation 120) the confirmation message from the DMS indicating that the manually entered radiation dose data has been received by the DMS. The method 200 ends.

By executing the method 200, the RMET 150 may increase a data storage ability of the DMS 140, may decrease network traffic and thus increase an efficiency of data transmission, and may increase a quality of medical data. For example, the DMS 140 may be enabled to store medical information and radiation dose data from irradiating modalities which are not in direct communication with the DMS 140, thus enabling the radiation dose data from these imaging modalities to be stored in a standardized format. This may increase an accessibility of the radiation dose data by third-party tools. Additionally, as further described herein, the RMET 150 may be adjusted to different operating modes based on medical environment conditions, such as data format configurations of the DMS 140 and/or the RIS 130, which may increase an efficiency of the RMET 150 and the medical environment by decreasing data transmission time. This may further reduce network traffic, as the RMET 150 may transmit outputs to the RIS 130 and the DMS 140 in formats usable thereby, as further described herein.

FIGS. 7-12 provide three example scenarios wherein operation of the RMET 150 may be adjusted to correspond with a type of data format used by the DMS 140 and/or the RIS 130. For example, elements of the worklist access component series 152 and/or the data submission component series 154, such as the DICOM® MWL collector 158 and the DICOM® SR generator 164, are configured to operably couple the RMET 150 to the RIS 130 and the DMS 140, respectively, when the RIS 130 and the DMS 140 are configured with the DICOM® standard. In medical environment configurations where the RIS 130 and the DMS 140 are not configured with the DICOM® standard, the DICOM® MWL collector 158 and the DICOM® SR generator 164 may be omitted from the RMET 150 or included in the RMET 150, but are inactive, as described with respect to FIGS. 1-2B. This may assist in reducing a processing demand of the RMET 150 and/or reducing a time of data transmission to the DMS 140.

FIG. 7 shows a first example configuration of a DICOM®-based manual entry method 700. The method 700 may be an adaptation of the method 200 of FIGS. 2A-2B and may be implemented by the RMET 150 when the RIS 130 and the DMS 140 both comprise DICOM® standards for transmitting and receiving data. For example, the RIS 130 comprises a DICOM® modality worklist component 710 and the DMS 140 comprises a DICOM® listener SCP 720. All components of the RMET 150 described with respect to FIG. 1 may be active/loaded onto the server 110 and used to transform user inputs from a first format (e.g., HTML) to a second format (e.g., FHIR® standard), and from the second format to a third format (e.g., DICOM® standard), such that a modality worklist may be retrieved from the RIS 130 and manually entered data may be submitted to the DMS 140. The RMET 150 may execute at least part of the method 200, as described with respect to FIGS. 2A-2B, the RIS 130 may execute at least part of the method 300, as described with respect to FIG. 3, and the DMS 140 may execute at least part of the method 400, as described with respect to FIG. 4.

A user may interact with the workstation 120 to submit the first user input to the RMET 150. The workstation 120 may transmit the first user input, formatted as HTML, to the RMET 150 via the network of the medical environment 100 (1). For example, the RMET 150 may communicate with the workstation 120 through Hypertext Transfer Protocol (HTTP). The HTML worklist access component 156 of the RMET 150 may receive the first user input in the HTML format, transform the first user input from the HTML format (e.g., the first format) to a FHIR® service request (e.g., the second format), and send the first user input in the second format to the DICOM® MWL collector 158 (2). As briefly described above, it may be known that the DMS 140 and the RIS 130 are configured to communicate using the DICOM® standard. The DICOM® MWL collector transforms the first input from the FHIR® service request (e.g., the second format) to a DICOM® modality worklist (MWL) query (e.g., the third format), and transmits the first input in the third format to the RIS 130 (3). The RIS 130 comprises the DICOM® modality worklist component 710 and, as described with respect to FIG. 3, the RIS 130 may receive the MWL query (e.g., the first user input in the third format), locate and retrieve the requested modality worklist in a memory of the RIS 130, and transmit the requested modality worklist to the RMET 150. For example, the requested modality worklist may be transmitted to the DICOM® MWL collector of the RMET 150 as a MWL response. The requested modality worklist may be output for display, for example, on the UI 122 of the workstation 120 (e.g., as shown in FIG. 5).

A user may interact with the workstation 120 to submit the second user input to the RMET 150. For example, as described with respect to FIGS. 2A-2B and 5-6, the user may select a procedure from the requested modality worklist displayed on the UI 122 of the workstation 120 and submit radiation dose information for the selected procedure (a). In some examples, more radiation dose information may be submitted for more than one procedure of the modality worklist in the second user input. The second user input may be submitted in the first format (e.g., HTML) and may be received by the radiation manual entry POST component 162 of the RMET 150, which is configured to convert information of the second user input from HTML to a FHIR® observation (e.g., the second format). The radiation manual entry POST component 162 may then post (e.g., send) the second user input as the FHIR® observation to the DICOM® SR generator 164 of the RMET 150 (*b*). The DICOM® SR generator 164 transforms the second user input from the FHIR® observation (e.g., the second format) to a DICOM® SR (e.g., the third format), and transmits the second user input as the DICOM® SR from the RMET 150 to the DMS 140, where the DICOM® SR may be received by the DICOM® listener SCP 720 of the DMS 140 (*c*). For example, the DICOM® SR generator 164 may execute a C-store protocol to transmit the DICOM® SR to the DMS 140 and direct the DMS 140 to store the DICOM® SR. In response to receiving and storing the second user input (e.g., as the DICOM® SR), the DMS 140 may send a message to the RMET 150, the message confirming receipt of the manually entered radiation dose data for one or more scheduled procedures of the modality worklist. For example, the message may include at least one of an audio, visual, and/or text-based data indicating that manually entered radiation dose information for the scheduled procedure of the requested modality worklist (e.g., the second user input) has been received by the DMS 140.

Turning to FIG. 8, a sequence diagram 800 illustrating transformation and transmission of data by elements of the medical environment 100, as described with respect to FIG. 7, is shown. Elements of FIG. 7 which are included in FIG. 8 are similarly named and numbered. FIG. 8 describes an embodiment of the disclosed systems and methods where the first format for data is HTML, the second format is FHIR®, and the third format is DICOM®, and where the RIS 130 and the DMS 140 each comprise elements with the DICOM® standards. In other embodiments, one or more different formats and associated query and response protocols may be used.

At 802, a user may access the front-end of the RMET 150, through a user desktop (e.g., the workstation 120), to access a scheduled worklist of procedures. Accessing the front-end of the RMET 150 includes submitting a first user input requesting access to a modality worklist stored in the RIS 130. The HTML worklist access component 156 transforms the first user input from the first format (e.g., HTML) to the second format (e.g., FHIR®). At 804, a front-end component of the RMET 150 makes a request of a back-end component of the RMET 150. Specifically, the HTML worklist access component 156 may make a FHIR® SEARCH query on ServiceRequest resources to the DICOM® MWL Collector 158. The FHIR® SEARCH query is related to a FHIR® ServiceRequest search, as described with respect to FIG. 7. For example, the collected FHIR® ServiceRequest resources can follow an analysis done by HL7® for mapping HL7® V2 messages and DICOM® MWL messages to an imaging service request. At 806, the DICOM® MWL Collector 158 makes a MWL C-FIND-QR (e.g., transforms the first user input from the second format to the third format) to collect the requested modality worklist from the RIS 130, based on parameters provided in the FHIR® ServiceRequest query (e.g., the first user input). The DICOM® MWL Collector 158 may be configured to perform periodic query to the DICOM® modality worklist component 710 of the RIS 130 to periodically collect and cache details of scheduled procedures stored in modality worklists of the RIS 130. At 808, the RIS 130 transmits a DICOM® MWL response, including a requested modality worklist, to the DICOM® MWL collector 158. The DICOM® MWL collector 158 converts the DICOM® MWL response to a bundle of ServiceRequest resources in the FHIR® standard (e.g., FHIR® ServiceRequest) and, at 810, transmits the FHIR® ServiceRequest to the front-end of the RMET 150 (e.g., the HTML worklist access component 156). At 812, the FHIR® ServiceRequest is converted to the first format (e.g., HTML) by the HTML worklist access component 156 and is output for display at the display device 124 of the workstation 120.

At 814, the user selects a scheduled procedure (e.g., an entry from the requested modality worklist) and manually enters radiation dose data for the selected scheduled procedure in an HTML form (e.g., the second example display 600) via the UI 122 of the workstation 120. Content of the HTML form is submitted to the radiation manual entry (ME) POST component 162 at 816, where the content (e.g., the second user input) is translated into a FHIR® observation resource (e.g., the second format). The FHIR® observation resource may include radiation dose summary resources containing radiation information which is sufficient to report radiation dose data related to a procedure. At 818, a HTTP FHIR® POST with the Observation resource is sent to the DICOM® SR generator. The Observation resource follows FHIR® and HL7® standards regarding sharing radiation data with FHIR®. At 820, the DICOM® SR Generator 164 generates a DICOM® SR object, based on the FHIR® observation resource received from the front-end application. Herein mapping is performed from FHIR® observation to DICOM® SR. The DICOM® SR object is sent to the DCM listener SCP 720 of the DMS 140. A response (e.g., confirmation message) is sent to the workstation 120 from the DMS 140, indicating that the form submission with radiation data was well considered. For example, at 822, a DCM C-STORE-RSP (response) is sent from the DMS 140 to the DICOM® SR Generator 164 of the RMET 150, the DCM C-STORE-RSP is translated to a FHIR® response at 824 and transmitted to the front-end of the RMET 150, and returned to the workstation 120 at 826 for display.

In this way, the RMET 150 enables manual entry of radiation dose data into the DMS 140, thus allowing radiation dose data collected by irradiating modalities not configured with output standards used by the DMS 140 to be stored by the DMS 140. The RMET 150 enables submission of radiation information to the DMS 140 without using a manual entry tool of the DMS 140 which either doesn't exist or is proprietary to the DMS 140. This increases a storage ability of the DMS 140, where the DMS 140 may be enabled to accept radiation data inputs manually entered into the RMET 150 regardless of an original data format of the radiation data. For example, through use of the RMET 150 described herein, the DMS 140 may receive a greater number of radiation dose data inputs than the DMS 140 may accept without use of the RMET 150.

In the example of FIGS. 7 and 8, all components of the RMET 150 described with respect to FIG. 1 are used to acquire a modality worklist and submit dose information to the DMS 140. As further described with respect to FIGS. 9-12, when the RIS 130 and/or the DMS 140 use a data format configuration other than DICOM®, some components of the RMET 150 may not be used to retrieve the worklist and/or submit radiation dose data.

Turning to FIG. 9, a second example configuration is shown of a FHIR® and DICOM®-based manual entry method 900. This method may be an adaptation of the method 200 of FIGS. 2A and 2B, and may be implemented by the RMET 150 when the RIS 130 comprises FHIR® standards and the DMS 140 comprises DICOM® standards for transmitting and receiving data. For example, the RIS 130 comprises a FHIR®-based MWL server 910 and the DMS 140 comprises the DICOM® listener SCP 720. Since the RIS 130 is configured to receive transmissions formatted according to FHIR® standards, components of the worklist access component series 152 used to convert the first user input from FHIR® standard to DICOM® standard (e.g., the DICOM® MWL collector 158) may be turned off or excluded from the RMET 150. The RMET 150 may execute at least part of the method 200, as described with respect to FIGS. 2A-2B, the RIS 130 may execute at least part of the method 300, as described with respect to FIG. 3, and the DMS 140 may execute at least part of the method 400, as described with respect to FIG. 4.

A user may interact with the workstation 120 to submit the first user input to the RMET 150. The workstation 120 may transmit the first user input, formatted as HTML, to the RMET 150 via the network of the medical environment 100 (1). The HTML worklist access component 156 of the RMET 150 may receive the first user input in the HTML format, transform the first user input from the HTML format (e.g., the first format) to a FHIR® ServiceRequest query (e.g., the second format), and send the first user input in the second format to the RIS 130 (2). As briefly described above, it may be known that the RIS 130 is configured to communicate using the FHIR® standard. For example, during loading/setup of the RMET 150, it may be indicated to the RMET 150 that the RIS 130 comprises the FHIR®-based MWL server 910. The DICOM® MWL collector 158 of the back-end of the RMET 150 may be inactive, thus reducing processing work of the RMET 150. As described with respect to FIG. 3, the RIS 130 may receive the FHIR® ServiceRequest query (e.g., the first user input in the second format), locate and retrieve the requested modality worklist in a memory of the RIS 130, and transmit the requested modality worklist to the RMET 150. The requested modality worklist may be output for display, for example, on the UI 122 of the workstation 120 (e.g., as shown in FIG. 5).

A user may interact with the workstation 120 to submit the second user input to the RMET 150. For example, as described with respect to FIGS. 2A-2B and 5-6, the user may select a procedure from the requested modality worklist displayed on the UI 122 of the workstation 120 and submit radiation dose information for the selected procedure (a). In some examples, more radiation dose information may be submitted for more than one procedure of the modality worklist in the second user input. The second user input may be submitted in the first format (e.g., HTML) and may be received by the radiation manual entry POST component 162 of the RMET 150, which is configured to convert information of the second user input from HTML to a FHIR® observation (e.g., the second format). The radiation manual entry POST component 162 may then post (e.g., send) the second user input as the FHIR® observation to the DICOM® SR generator 164 of the RMET 150 (b). The DICOM® SR generator 164 transforms the second user input from the FHIR® observation (e.g., the second format) to a DICOM® SR (e.g., the third format), and transmits the second user input as the DICOM® SR from the RMET 150 to the DMS 140, where the DICOM® SR may be received by the DICOM® listener SCP 720 of the DMS 140 (c). For example, the DICOM® SR generator 164 may execute a C-STORE protocol to transmit the DICOM® SR to the DMS 140 and direct the DMS 140 to store the DICOM® SR.

In response to receiving and storing the second user input (e.g., as the DICOM® SR), the DMS 140 may send a message to the RMET 150, the message confirming receipt of the manually entered radiation dose data for one or more scheduled procedures of the modality worklist.

Turning to FIG. 10, a second sequence diagram 1000 illustrating transformation and transmission of data by elements of the medical environment 100, as described with respect to FIG. 9, is shown. Elements of FIG. 9 which are included in FIG. 10 are similarly named and numbered. FIG. 10 describes an embodiment of the disclosed systems and methods where the first format for data is HTML, the second format is FHIR®, and the third format is DICOM®. The RIS 130 comprises elements with FHIR® standards and the DMS 140 comprises elements with the DICOM® standards. In other embodiments, one or more different formats and associated query and response protocols may be used.

The second sequence diagram 1000 is similar to the first sequence diagram 800 of FIG. 8, except for removal of operations 806 and 808, where the DICOM® MWL Collector 158 transforms the first user input from the second format to the third format and sends to the RIS 130 to collect the requested modality worklist, based on the parameters provided in the FHIR® ServiceRequest query. The second sequence diagram 1000 method is as follows. At 1002, the user, via the desktop (e.g., the workstation 120), accesses the front-end of the RMET 150 to access the scheduled worklist of procedures. Accessing the front-end of the RMET 150 includes submitting a first user input requesting access to a modality worklist stored in the RIS 130. The HTML worklist access component 156 transforms the first user input from the first format (e.g., HTML) to the second format (e.g., FHIR®). At 1004, a front-end component of the RMET 150 makes a FHIR® SEARCH query on ServiceRequest resources to the RIS 130 directly. For example, the HTML worklist access component 156 transmits the first user input in the second format (e.g., FHIR® ServiceRequest query) to the FHIR®-based MWL server 910 to collect the requested modality worklist from the RIS 130, based on parameters provided in the FHIR® ServiceRequest query (e.g., the first user input). At 1006, the retrieved modality worklist is returned from the RIS 130 to the front-end of the RMET 150 as a ServiceRequest bundle (e.g., FHIR® ServiceRequest). The HTML worklist access component 156 transforms the FHIR® ServiceRequest to an HTML response. At 1008, the retrieved modality worklist is returned to the workstation 120 as the HTML response and the requested modality worklist is output for display at the display device 124 of the workstation 120.

At 1010, the user selects an entry from the retrieved modality worklist and manually enters radiation dose data into an HTML form (e.g., the second example display 600) via the UI 122 of the workstation 120. Content of the HTML form is submitted to the radiation manual entry (ME) POST component 162 at 1012, where the content (e.g., the second user input) is translated into a FHIR® observation resource (e.g., the second format). The FHIR® observation resource may include radiation dose summary resources containing radiation information which is sufficient to report radiation dose data related to a procedure. At 1014, a HTTP FHIR® POST with the Observation resource is sent to the DICOM® SR generator. The Observation resource follows FHIR® and HL7® standards regarding sharing radiation data with FHIR®. At 1016, the DICOM® SR Generator 164 generates a DICOM® SR object, based on the FHIR® observation resource received from the front-end application. Herein mapping is performed from FHIR® observation to DICOM® SR. The DICOM® SR object is sent to the DCM listener SCP 720 of the DMS 140. A response (e.g., confirmation message) is sent to the workstation 120 from the DMS 140, indicating that the form submission with radiation data was well considered. For example, at 1018, a DCM C-STORE-RSP is sent from the DMS 140 to the DICOM® SR Generator 164 of the RMET 150, the DCM C-STORE-RSP is translated to a FHIR® response at 1020 and transmitted to the front-end of the RMET 150, and returned to the workstation 120 at 1022 for display.

In this way, the RMET 150 enables retrieval of a modality worklist from the RIS 130 and manual entry of radiation dose data into the DMS 140 when data format configurations of the RIS 130 and the DMS 140 are different. This increases an ability of the RIS 130 and the DMS 140 to receive data. When the data format configuration of the RIS 130 and the DMS 140 are known, and components of the RMET 150 are consequently activated and/or deactivated during operation of the RMET 150, a processing demand of the RMET 150 may decrease, compared to when all elements of the RMET 150 are active (e.g., as described with respect to FIGS. 2A-2B).

In the example of FIGS. 9 and 10, a back-end component of the RMET 150 which is used to operably connect the RMET 150 to a RIS comprising a data format configuration which is not included in the RIS 130 is omitted from operation and/or configuration of the RMET 150. As further described with respect to FIGS. 11 and 12, when the RIS 130 and the DMS 140 use a data format configuration other than DICOM®, components of the RMET 150 used to connect to RIS and DMS which comprise DICOM® elements (e.g., DICOM® modality worklist component 710 and DICOM® listener SCP 720, respectively) are omitted from the RMET 150. For example, in the embodiment of the RMET 150 described with respect to FIGS. 11 and 12, both back-end components (e.g., the DICOM® SR generator 164 and the DICOM® MWL collector 158) may not be used to retrieve the worklist and/or submit radiation dose data.

Turning to FIG. 11, a third example configuration is shown of a FHIR®-based manual entry method 1100. This method may be an adaptation of the method 200 of FIGS. 2A and 2B, and may be implemented by the RMET 150 when the RIS 130 and the DMS 140 comprise FHIR® standards for transmitting and receiving data. For example, the RIS 130 comprises a FHIR®-based MWL server 910 and the DMS 140 comprises a FHIR®-based radiation server 1110. Since neither the DMS 140 nor the RIS 130 are configured to receive transmissions formatted according to DICOM® standards, components of the RMET 150 used to convert the first input and the second input to the third format (e.g., DICOM®) may be turned off or excluded from the RMET 150. Front-end components of the RMET 150 may directly communicate with the RIS 130 and the DMS 140. For example, the HTML worklist access component 156 may directly communicate with the RIS 130 and the radiation manual entry POST component 162 may directly communicate with the DMS 140. The RMET 150 may execute at least part of the method 200, as described with respect to FIGS. 2A-2B, the RIS 130 may execute at least part of the method 300, as described with respect to FIG. 3, and the DMS 140 may execute at least part of the method 400, as described with respect to FIG. 4.

A user may interact with the workstation 120 to submit the first user input to the RMET 150. The workstation 120 may transmit the first user input, formatted as HTML, to the RMET 150 via the network of the medical environment 100 (1). The HTML worklist access component 156 of the RMET 150 may receive the first user input in the HTML format, transform the first user input from the HTML format (e.g., the first format) to a FHIR® ServiceRequest query (e.g., the second format), and send the first user input in the second format to the RIS 130 (2). As briefly described above, it may be known that the RIS 130 is configured to communicate using the FHIR® standard. For example, during loading/setup of the RMET 150, it may be indicated to the RMET 150 that the RIS 130 comprises the FHIR®-based MWL server 910. The DICOM® MWL collector 158 of the back-end of the RMET 150 may be inactive, thus reducing processing work of the RMET 150. As described with respect to FIG. 3, the RIS 130 may receive the FHIR® ServiceRequest query (e.g., the first user input in the second format), locate and retrieve the requested modality worklist in a memory of the RIS 130, and transmit the requested modality worklist to the RMET 150. The requested modality worklist may be output for display, for example, on the UI 122 of the workstation 120 (e.g., as shown in FIG. 5).

A user may interact with the workstation 120 to submit the second user input to the RMET 150. For example, as described with respect to FIGS. 2A-2B and 5-6, the user may select a procedure from the requested modality worklist displayed on the UI 122 of the workstation 120 and submit radiation dose information for the selected procedure (a). In some examples, more radiation dose information may be submitted for more than one procedure of the modality worklist in the second user input. The second user input may be submitted in the first format (e.g., HTML) and may be received by the radiation manual entry POST component 162 of the RMET 150, which is configured to convert information of the second user input from HTML to a FHIR® observation (e.g., the second format). The radiation manual entry POST component 162 may then post (e.g., send) the second user input as the FHIR® observation to a FHIR®-based radiation server 1110 of the DMS 140 (b). In response to receiving and storing the second user input (e.g., as the FHIR® observation), the DMS 140 may send a message to the RMET 150, the message confirming receipt of the manually entered radiation dose data for one or more scheduled procedures of the modality worklist.

Turning to FIG. 12, a third sequence diagram 1200 illustrating transformation and transmission of data by elements of the medical environment 100, as described with respect to FIG. 11, is shown. Elements of FIG. 11 which are included in FIG. 12 are similarly named and numbered. FIG. 11 describes an embodiment of the disclosed systems and methods where the first format for data is HTML, the second format is FHIR®, and the third format is DICOM®, and where both the RIS 130 and the DMS comprise elements with FHIR® standards. In other embodiments, one or more different formats and associated query and response protocols may be used.

The third sequence diagram 1200 is similar to the second sequence diagram 1000 of FIG. 10, except for removal of operations 1016 and 1018, where the DICOM® SR generator 164 transforms the second user input from the second format to the third format and sends the second user input in the format to the DMS 140 to submit the manually entered radiation dose data. The third sequence diagram method is as follows. At 1202, the user, via the desktop (e.g., the workstation 120), accesses the front-end of the RMET 150 to access the scheduled worklist of procedures. Accessing the front-end of the RMET 150 includes submitting a first user input requesting access to a modality worklist stored in the RIS 130. The HTML worklist access component 156 transforms the first user input from the first format (e.g., HTML)

to the second format (e.g., FHIR®). At 1204, a front-end component of the RMET 150 makes a FHIR® SEARCH query on ServiceRequest resources to the RIS 130 directly. For example, the HTML worklist access component 156 transmits the first user input in the second format (e.g., FHIR® ServiceRequest query) to the FHIR®-based MWL server 910 to collect the requested modality worklist from the RIS 130, based on parameters provided in the FHIR® ServiceRequest query (e.g., the first user input). At 1206, the retrieved modality worklist is returned from the RIS 130 to the front-end of the RMET 150 as a ServiceRequest bundle (e.g., FHIR® ServiceRequest). The HTML worklist access component 156 transforms the FHIR® ServiceRequest to an HTML response. At 1208, the retrieved modality worklist is returned to the workstation 120 as the HTML response and the requested modality worklist is output for display at the display device 124 of the workstation 120.

At 1210, the user selects an entry from the retrieved modality worklist and manually enters radiation dose data into an HTML form (e.g., the second example display 600) via the UI 122 of the workstation 120. Content of the HTML form is submitted to the radiation manual entry (ME) POST component 162 at 1212, where the content (e.g., the second user input) is translated into a FHIR® observation resource (e.g., the second format). The FHIR® observation resource may include radiation dose summary resources containing radiation information which is sufficient to report radiation dose data related to a procedure. At 1214, a HTTP FHIR® POST with the Observation resource is sent to the FHIR®-based radiation server 1110 of the DMS 140 directly. A response (e.g., confirmation message) is sent to the workstation 120 from the DMS 140, indicating that the form submission with radiation data was well considered. For example, at 1216, a FHIR® response is transmitted to the front-end of the RMET 150, and returned to the workstation 120 at 1218 for display.

In this way, the RMET 150 enables manual entry of radiation dose data into the DMS 140, thus allowing radiation dose data collected by irradiating modalities not configured with output standards used by the DMS 140 to be stored by the DMS 140. The RMET 150 enables submission of radiation information to the DMS 140 without using a manual entry tool of the DMS 140 which either doesn't exist or is proprietary to the DMS 140. As only components of the RMET 150 which correspond to data format configurations of the DMS 140 and the RIS 130 are active, a processing and memory demand of the RMET 150 may decrease, compared to when all elements of the RMET 150 are active (e.g., as described with respect to FIGS. 2A-2B).

Technical effects of the systems and methods described herein include increased data storage ability of a DMS. The RMET, via the methods described herein, enables agnostic transmission of manually entered radiation dose data collected by irradiating modalities which may or may not comprise outputs having standard data format configurations, such as those used by RIS and/or DMS. Data format-related constraints on data that may be stored in the DMS may thus be removed. Use of the RMET may decrease data transmission times, decrease network traffic, decrease time between irradiating events and retrieval/use of radiation dose data from the DMS by third-party tools, and increase a quantity and accuracy of manually entered data stored in the DMS. Additionally, the RMET may be used in different configurations to further decrease data transmission time and decrease processing power of servers and processors hosting and executing methods of the RMET.

The disclosure also provides support for a radiation manual entry tool (RMET), comprising: a worklist access component series configured to receive via a network a first user input requesting access to a modality worklist, transform the first user input from a first format to a second format, transmit the first user input in the second format via the network, and receive a requested modality worklist via the network, and a data submission component series configured to receive via the network a second user input including radiation dose information manually entered into the requested modality worklist, transform the second user input from the first format to the second format, transmit the second user input via the network, and receive a message via the network confirming receipt of manually entered radiation dose information for a scheduled procedure of the requested modality worklist. In a first example of the system, the worklist access component series is further configured to transform the first user input from the second format to a third format in response to the worklist access component series not receiving the requested modality worklist following transmission of the first user input in the second format. In a second example of the system, optionally including the first example, the worklist access component series comprises a HyperText Markup Language (HTML) worklist access component configured to receive the first user input in the first format, transform the first user input from the first format to the second format, and output the first user input in the second format. In a third example of the system, optionally including one or both of the first and second examples, the worklist access component series further comprises a Digital Imaging and Communications in Medicine (DICOM®) modality worklist (MWL) collector configured to receive the first user input in the second format from the HTML worklist access component, transform the first user input from the second format to a third format, and output the first user input in the third format. In a fourth example of the system, optionally including one or more or each of the first through third examples, the data submission component series is further configured to transform the second user input from the second format to a third format in response to the data submission component series not receiving the message confirming receipt of manually entered radiation dose information for the scheduled procedure following transmission of the second user input in the second format. In a fifth example of the system, optionally including one or more or each of the first through fourth examples, the data submission component series comprises a radiation manual entry POST component configured to receive the second user input in the first format, transform the second user input from the first format to the second format, and output the second user input in the second format. In a sixth example of the system, optionally including one or more or each of the first through fifth examples, the data submission component series further comprises a Digital Imaging and Communications in Medicine (DICOM®) structured report (SR) generator configured to receive the second user input in the second format from the radiation manual entry POST component, transform the second user input from the second format to a third format, and output the second user input in the third format. In a seventh example of the system, optionally including one or more or each of the first through sixth examples, the message comprises at least one of an audio, visual, and/or text-based data indicating that manually entered radiation dose information for the scheduled procedure of the requested modality worklist has been received by a dose management system (DMS).

The disclosure also provides support for a method for a radiation manual entry tool (RMET), comprising: receiving, via a network, a first user input in a first format comprising a standard markup language, the first user input requesting access to a modality worklist, transforming the first user input in the first format to a second format comprising a standard for medical data transmission, transmitting the first user input in the second format via the network to access a requested modality worklist, receiving the requested modality worklist via the network, receiving a second user input in the first format via the network, the second user input including manually entered radiation dose information for a scheduled procedure of the requested modality worklist, transforming the second user input in the first format to the second format, transmitting the second user input in the second format via the network to submit the manually entered radiation dose information for the scheduled procedure of the modality worklist, and receiving a message confirming receipt of the manually entered radiation dose information for the scheduled procedure. In a first example of the method, the first format is HyperText Markup Language (HTML) or another standard markup language. In a second example of the method, optionally including the first example, the second format is Fast Healthcare Interoperability Resources (FHIR®) or other standard for medical data transmission. In a third example of the method, optionally including one or both of the first and second examples, the method further comprises, in response to not receiving the requested modality worklist following transmission of the first user input in the second format, transforming the first user input in the second format to a third format and transmitting the first user input in the third format. In a fourth example of the method, optionally including one or more or each of the first through third examples, the third format is Digital Imaging and Communications in Medicine (DICOM®) or other standard for medical data transmission. In a fifth example of the method, optionally including one or more or each of the first through fourth examples, the method further comprises, in response to not receiving the message confirming receipt of the manually entered radiation dose information for the scheduled procedure, transforming the second user input in the second format to the third format and transmitting the second user input in the third format.

The disclosure also provides support for a system, comprising: a user input system implemented at a workstation, a radiology information system (RIS) stored at a first location, a dose management system (DMS) stored at a second location and a radiation manual entry tool (RMET) stored at a server communicably coupled to each of the RIS, the DMS, and the user input system via a network, and remote from each of the first location and the second location, the RMET including instructions to: receive a first user input in a first format requesting access to a modality worklist from the user input system, transform the first user input to a second format and/or a third format, transmit the first user input to the RIS via the network, receive a requested modality worklist from the RIS, receive from the workstation via the network a second user input in the first format, the second user input including manually entered radiation dose information for a scheduled procedure of the requested modality worklist, transforming the second user input in the first format to the second format and/or the third format, transmit information from the second user input to the DMS via the network, and receive a message from the DMS confirming receipt of the manually entered radiation dose information for the scheduled procedure. In a first example of the system, the first format is a standard markup language. In a second example of the system, optionally including the first example, the second format is a first standard for medical data transmission and the third format is a second standard for medical data transmission. In a third example of the system, optionally including one or both of the first and second examples, each of the DMS and the RIS uses the first standard for medical data transmission or the second standard for medical data transmission. In a fourth example of the system, optionally including one or more or each of the first through third examples, the DMS is configured to receive the second user input in the second format and/or the third format and transmit the message confirming receipt of the manually entered radiation dose information for the scheduled procedure. In a fifth example of the system, optionally including one or more or each of the first through fourth examples, the RIS is configured to receive the first user input in the second format and/or the third format and transmit the requested modality worklist.

Elements of the medical environment 100 and of configurations 700-1200 may communicate with each other via a network, which may be a suitable wired and/or wireless network. One or more of the devices described herein may be implemented over a cloud or other computer network. A communication module of the RMET facilitates transmission of electronic data within and/or among one or more systems. Communication via the communication module can be implemented using one or more protocols. In some examples, communication via the communication module occurs according to one or more standards (e.g., HL7®, ANSI X12N, etc.). Communication can be via a wired interface (e.g., a data bus, a Universal Serial Bus (USB) connection, etc.) and/or a wireless interface (e.g., radio frequency, infrared, near field communication (NFC), etc.). For example, the communication module may communicate via wired local area network (LAN), wireless LAN, wide area network (WAN), etc. using any past, present, or future communication protocol (e.g., BLUETOOTH™, USB 2.0, USB 3.0, etc.). The RMET may further include memory including one or more data storage structures, such as optical memory devices, magnetic memory devices, or solid-state memory devices, for storing programs and routines executed by processor(s) to carry out various functionalities disclosed herein. Memory may include any desired type of volatile and/or non-volatile memory such as, for example, static random access memory (SRAM), dynamic random access memory (DRAM), flash memory, read-only memory (ROM), etc. A processor(s) of the RMET may be any suitable processor, processing unit, or microprocessor, for example. Processor(s) may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

In this way, a new methodology to implement manually entered radiation data is provided. The method has standard based communication with the hospital components, opposed to proprietary communication. The method is agnostic to the dose management system, thus providing a vendor-neutral solution. The method is a light, agnostic, and standardized solution using the latest healthcare technologies.

As used herein, an element or step recited in the singular and preceded with the word "a" or "an" should be understood as not excluding plural of said elements or steps, unless such exclusion is explicitly stated. Furthermore, references to "one example" of the present invention are not intended to be interpreted as excluding the existence of additional examples that also incorporate the recited features. Moreover, unless explicitly stated to the contrary, examples "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A radiation manual entry tool (RMET), comprising:
a worklist access component series configured to receive via a network a first user input requesting access to a modality worklist, transform the first user input from a first format to a second format, transmit the first user input in the second format to a radiology information system via the network, and receive the modality worklist in the first format from the radiology information system via the network; and
a data submission component series configured to receive via the network a second user input including radiation dose information manually entered into the modality worklist, transform the second user input from the first format to the second format, transmit the second user input in the second format to a dose management system via the network, and receive a message via the network confirming receipt of manually entered radiation dose information for a scheduled procedure of the modality worklist.

2. The RMET of claim 1, wherein the worklist access component series is further configured to transform the first user input from the second format to a third format in response to the worklist access component series not receiving the modality worklist following transmission of the first user input in the second format, and wherein the first format enables display and modification of data in a text-based format, the second format enables medical image data transmission, and the third format enables clinical data transmission.

3. The RMET of claim 1, wherein the worklist access component series comprises a HyperText Markup Language (HTML) worklist access component configured to receive the first user input in the first format, transform the first user input from the first format to the second format, and output the first user input in the second format.

4. The RMET of claim 3, wherein the worklist access component series further comprises a Digital Imaging and Communications in Medicine (DICOM®) modality worklist (MWL) collector configured to receive the first user input in the second format from the HTML worklist access component, transform the first user input from the second format to a third format, and output the first user input in the third format.

5. The RMET of claim 1, wherein the data submission component series is further configured to transform the second user input from the second format to a third format in response to the data submission component series not receiving the message confirming receipt of manually entered radiation dose information for the scheduled procedure following transmission of the second user input in the second format.

6. The RMET of claim 1, wherein the data submission component series comprises a radiation manual entry POST component configured to receive the second user input in the first format, transform the second user input from the first format to the second format, and output the second user input in the second format.

7. The RMET of claim 6, wherein the data submission component series further comprises a Digital Imaging and Communications in Medicine (DICOM®) structured report (SR) generator configured to receive the second user input in the second format from the radiation manual entry POST component, transform the second user input from the second format to a third format, and output the second user input in the third format.

8. The RMET of claim 1, wherein the message comprises at least one of an audio, visual, and text-based data indicating that manually entered radiation dose information for the scheduled procedure of the modality worklist has been received by the dose management system (DMS).

9. A method for a radiation manual entry tool (RMET), comprising:

receiving, via a network, a first user input in a first format comprising a standard markup language, the first user input requesting access to a modality worklist;

transforming the first user input in the first format to a second format comprising a standard for medical data transmission;

transmitting the first user input in the second format via the network to a radiology information system to access the modality worklist stored at the radiology information system;

receiving the modality worklist in the first format from the radiology information system via the network;

receiving a second user input in the first format via the network, the second user input including manually entered radiation dose information for a scheduled procedure of the modality worklist;

transforming the second user input in the first format to the second format;

transmitting the second user input in the second format to a dose management system via the network to submit the manually entered radiation dose information for the scheduled procedure of the modality worklist; and receiving a message confirming receipt of the manually entered radiation dose information for the scheduled procedure.

10. The method of claim 9, wherein the first format is HyperText Markup Language (HTML) or another standard markup language that enables display and modification of information in the first format at a front end of the RMET; wherein the first user input is received via user modification of a first display, including via selection of one or more filters that differentiate among different patients, study date and time, device, and dose status; and wherein the modality worklist is displayed in the first format on a display of the RMET, and the second user input is generated from modification of a second display including the modality worklist via adding or adjusting one or more text or numeric values of the modality worklist.

11. The method of claim 9, wherein the second format is Fast Healthcare Interoperability Resources (FHIR®) or other standard for medical data transmission, and wherein the first user input is transformed from the first format to the second format at a front end of the RMET, the modality worklist is transmitted to the front end of the RMET in the first format, the second user input is transformed from the first format to a third format and transmitted from the front end of the RMET to a back end of the RMET, and transmitted from the back end of the RMET in the third format to the dose management system.

12. The method of claim 9, further comprising, in response to not receiving the modality worklist following transmission of the first user input in the second format, transforming the first user input in the second format to a third format and transmitting the first user input in the third format.

13. The method of claim 12, wherein the third format is Digital Imaging and Communications in Medicine (DICOM®) or other standard for medical data transmission.

14. The method of claim 13, further comprising, in response to not receiving the message confirming receipt of the manually entered radiation dose information for the scheduled procedure, transforming the second user input in the second format to the third format and transmitting the second user input in the third format.

15. A system, comprising:

a user input system implemented at a workstation;

a radiology information system (RIS) stored at a first location;

a dose management system (DMS) stored at a second location; and a radiation manual entry tool (RMET) stored at a server communicably coupled to each of the RIS, the DMS, and the user input system via a network, and remote from each of the first location and the second location, the RMET including instructions to:

receive a first user input in a first format from the user input system requesting access to a modality worklist stored at the RIS;

transform the first user input to a second format or a third format;

transmit the first user input in the second format, the third format, or a combination of the second format and the third format to the RIS via the network;

receive the modality worklist from the RIS;

receive from the workstation via the network a second user input in the first format, the second user input including manually entered radiation dose information for a scheduled procedure of the modality worklist;

transform the second user input in the first format to the second format or the third format;

transmit the second user input in the second format, the third format, or a combination of the second format and the third format to the DMS via the network; and receive a message from the DMS confirming receipt of the manually entered radiation dose information for the scheduled procedure.

16. The system of claim 15, wherein the first format is a standard markup language, and wherein the RMET includes a front-end including a HyperText Markup Language (HTML) worklist access component configured to transform the first user input from the second format and transmit to a back-end of the RMET, including a modality worklist collector.

17. The system of claim 15, wherein the second format is a first standard for medical data transmission and the third format is a second standard for medical data transmission, and wherein transmitting the first user input in the second format includes sending a search/service request to a modality worklist server configured to operate in the second format, and receiving a service request bundle from the modality worklist server in the first format.

18. The system of claim 17, wherein each of the DMS and the RIS uses the first standard for medical data transmission or the second standard for medical data transmission.

19. The system of claim 15, wherein the DMS is configured to receive the second user input in the second format or the third format and transmit the message confirming receipt of the manually entered radiation dose information for the scheduled procedure.

20. The system of claim 15, wherein the RIS is configured to receive the first user input in the second format or the third format and transmit the modality worklist.

* * * * *